US006465250B1

(12) United States Patent
Wyatt

(10) Patent No.: US 6,465,250 B1
(45) Date of Patent: Oct. 15, 2002

(54) ANTISENSE MODULATION OF PROTEIN PHOSPHATASE 2 CATALYTIC SUBUNIT ALPHA EXPRESSION

(75) Inventor: Jacqueline Wyatt, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/780,049

(22) Filed: Feb. 9, 2001

(51) Int. Cl.[7] .......................... C12Q 1/68; C07H 21/04; C12N 15/85
(52) U.S. Cl. .......................... 435/375; 435/6; 435/91.1; 435/325; 435/366; 536/23.1; 536/24.31; 536/24.33; 536/24.5
(58) Field of Search .......................... 435/6, 325, 366, 435/375; 536/23.1, 24.5; 514/44

(56) References Cited

U.S. PATENT DOCUMENTS

| | | | |
|---|---|---|---|
| 5,700,821 A | 12/1997 | Lazo et al. | 514/374 |
| 5,925,660 A | 7/1999 | Lazo et al. | 514/374 |
| 5,948,902 A | * 9/1999 | Honkanen et al. | 536/24.5 |

FOREIGN PATENT DOCUMENTS

| | | |
|---|---|---|
| WO | WO 97/37037 | 10/1997 |
| WO | WO 98/14606 | 4/1998 |
| WO | WO 99/27134 | 6/1999 |

OTHER PUBLICATIONS

Inpyo Choi et al., Roles of protein phosphatase 2A in IL–6 signal transduction in Hep3B cells, Immunology Letters, 61, 1998, pp. 103–107.*
Douglas W. Green et al., Antisense Oligonucleotides: An Evolving Technology for the Modulation of Gene Expression in Human Disease, American College of Surgeons, pp. 93–105.*
Kuang–Yu Jen et al., Suppression of Gene Expression by Targeted Disruption of Messenger RNA: Available Options and Current Stategies, Stem Cells, 2000, pp. 307–319.*
Sudhir Agrawal et al., Antisense therapeutics: is it as simple as complementary base recognition? Molecular Medicine Today, Feb. 2000, vol. 6, pp. 72–81.*
D.D.F. Ma et al., Synthetic oligonucleotides as therapeutics: the coming of age, Biotechnology Annual Review, vol. 5, pp. 155–196.*
Andrea D. Branch, A good antisense molecule is hard to find, TIBS 23—Feb. 1998, pp. 45–50.*
W. Michael Flanagan et al., Cellular penetration and antisense activity by a phenoxazine–substituted heptanucleotide, Research, pp. 1–5.*
C. Frank Bennett et al., Pharmacology of Antisense Therapeutic Agents, pp. 13–46.*

Dobrowsky et al., Ceramide activates heterotrimeric protein phosphatase 2A, J. Biol. Chem., 1993, 268:15523–15530.
Goldberg, Protein phosphotase 2A: who shall regulate the regulator?, Biochem. Pharmacol., 1999, 57:321–328.
Gotz et al., Delayed embryonic lethality in mice lacking protein phosphotase 2A catalytic subunit Calpha, Proc. Natl. Acad. Sci. U. S. A., 1998, 95:12370–12375.
Khew–Goodall et al., Structure and transcriptional regulation of protein phosphatase 2A catalytic subunit genes, Biochemistry, 1991, 30:89–97.
Klarlund et al., An insulin–stimulated kemptide kinase purified from rat liver is deactivated by phosphatase 2A, J. Biol. Chem., 1991, 266:4052–4055.
Kowluru et al., Carboxylmethylation of the catalytic subunit of protein phosphatase 2A in insulin–secreting cells: evidence for functional consequences on enzyme activity and insulin secretion, Endocrinology, 1996, 137:2315–2323.
Millward et al., Regulation of protein kinase cascades by protein phosphatase 2A, Trends Biochem. Sci., 1999, 24:186–191.
Nishikawa et al., Expression of the catalytic and regulatory subunits of protein phosphatase type 2A may differentially modulated during retinoic acid–induced granulocytic differentiation of HL–60 cells, Cancer Res., 1994, 54–4879–4884.
Stone et al., The nucleotide sequence of the cDNA encoding the human lung protein phosphatase 2A alpha catalytic subunit, Nucleic Acids Res., 1988, 16:11365.
Tawara et al., Down–regulation by retinoic acid of the catalytic subunit of protein phosphatase type 2A during granulocytic differentiation of HL–60 cells, FEBS lett., 1993, 321:224–228.
Toyoda et al., Differential association of protein Ser/Thr phosphatase types 1 and 2A with the cytoskeleton upon platelet activation, Thromb. Haemost., 1996, 76:1053–1062.
Wera et al., Serine/threonine phosphatases, Biochemistry Journal, 1995, 311:17–29.
Zhang, Protein–tyrosine phosphatases: biological function, structural characteristics, and mechanism of catalysis, Crit. Rev. Biochem. Mol. Biol., 1998, 33:1–52.

* cited by examiner

Primary Examiner—John L. LeGuyader
Assistant Examiner—M Schmidt
(74) Attorney, Agent, or Firm—Licata & Tyrrell P.C.

(57) ABSTRACT

Antisense compounds, compositions and methods are provided for modulating the expression of Protein Phosphatase 2 catalytic subunit alpha. The compositions comprise antisense compounds, particularly antisense oligonucleotides, targeted to nucleic acids encoding Protein Phosphatase 2 catalytic subunit alpha. Methods of using these compounds for modulation of Protein Phosphatase 2 catalytic subunit alpha expression and for treatment of diseases associated with expression of Protein Phosphatase 2 catalytic subunit alpha are provided.

26 Claims, No Drawings

```
                           SEQUENCE LISTING

<160> NUMBER OF SEQ ID NOS: 96

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                                    20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                    20

<210> SEQ ID NO 3
<211> LENGTH: 2966
<212> TYPE: DNA
<213> ORGANISM: Homo sapiens
<220> FEATURE:
<221> NAME/KEY: CDS
<222> LOCATION: (995)...(1924)

<400> SEQUENCE: 3
aaccaccggc gaggagcggg gcgcgtggaa gcgagccgcg gtccgaggcc caaagaaaag          60
cccaagcctc gcccccgcca tcgcgcccga cgagacacct aggtccgggg acgggtgtgt         120
gccgcggaag tcaggtgcac tgcgcagcac tcccccggta ggtacacgct cctccaccta         180
cgagtgacct aattacaagg tgccagccgc gcccagaggt ggggggtggtt aatccaagcg        240 gccactcgct gcccgttcct gcccccaaag atgacggaaa cccacacgat tacagagccg         300
cagcacccca gatgagccac ggggtcgcaa ttctcgtttc cgtgatcgga ctgccaggcc         360
ccaggtgagg agctgagttc atcaccagag cggccttccc aggggaacca gttacaggct         420
gccagtggcc ccggcttcca tccggtctgc gcctgcgcgc ggcccaagcc ctcgcctctc         480
ctggaatagt gctcagggat tagtccggtt cgccgctgtg ccactgcgca tgctccagct         540
ccatccttcc cttcccccac caccccgccc tccgggagcc acgcccaaaa agtcaaggcg         600
cttcagttac cagccggcta cgtggcctgc gctttgaccc ccagtttgcg ccccaactcc         660
ggtcgtgcgg ccgcccgggg agggctctgc agttgcgcag cttgctcccc ggccctttc          720 ccctccgctc cccgccgcct cctgacgccg ggcgtgacgt caccacgccc ggcggccgcc         780
attacagaga gccgagctct ggagcctcag cgagcggagg aggaggcgca gggccgacgg         840
ccgagtactg cggtgagagc cagcgggcca gcgccagcct caacagccgc cagaagtaca         900
cgaggaaccg gcggcgcgt gtgcgtgtag gcccgtgtgc gggcggcggc gcgggaggag           960
cgcggagcgg cagccggctg gggcgggtgg catc atg gac gag aag gtg ttc acc        1015
                                   Met Asp Glu Lys Val Phe Thr
```

```
                        1                5
aag gag ctg gac cag tgg atc gag cag ctg aac gag tgc aag cag ctg    1063
ys  Glu Leu Asp Gln Trp Ile Glu Gln Leu Asn Glu Cys Lys Gln Leu
         10              15                  20 tcc gag tcc cag gtc aag agc ctc tgc gag aag gct aaa gaa atc ctg    1111
er  Glu Ser Gln Val Lys Ser Leu Cys Glu Lys Ala Lys Glu Ile Leu
     25                  30                  35 aca aaa gaa tcc aac gtg caa gag gtt cga tgt cca gtt act gtc tgt    1159
hr  Lys Glu Ser Asn Val Gln Glu Val Arg Cys Pro Val Thr Val Cys
40                  45                  50                  55 gga gat gtg cat ggg caa ttt cat gat ctc atg gaa ctg ttt aga att    1207
ly  Asp Val His Gly Gln Phe His Asp Leu Met Glu Leu Phe Arg Ile
             60                  65                  70 ggt ggc aaa tca cca gat aca aat tac ttg ttt atg gga gat tat gtt    1255
ly  Gly Lys Ser Pro Asp Thr Asn Tyr Leu Phe Met Gly Asp Tyr Val
         75                  80                  85 gac aga gga tat tat tca gtt gaa aca gtt aca ctg ctt gta gct ctt    1303
sp  Arg Gly Tyr Tyr Ser Val Glu Thr Val Thr Leu Leu Val Ala Leu
     90                  95                 100 aag gtt cgt tac cgt gaa cgc atc acc att ctt cga ggg aat cat gag    1351
ys  Val Arg Tyr Arg Glu Arg Ile Thr Ile Leu Arg Gly Asn His Glu
105                 110                 115 agc aga cag atc aca caa gtt tat ggt ttc tat gat gaa tgt tta aga    1399
er  Arg Gln Ile Thr Gln Val Tyr Gly Phe Tyr Asp Glu Cys Leu Arg
20                  125                 130                 135 aaa tat gga aat gca aat gtt tgg aaa tat ttt aca gat ctt ttt gac    1447
ys  Tyr Gly Asn Ala Asn Val Trp Lys Tyr Phe Thr Asp Leu Phe Asp
             140                 145                 150 tat ctt cct ctc act gcc ttg gtg gat ggg cag atc ttc tgt cta cat    1495
yr  Leu Pro Leu Thr Ala Leu Val Asp Gly Gln Ile Phe Cys Leu His
         155                 160                 165 ggt ggt ctc tcg cca tct ata gat aca ctg gat cat atc aga gca ctt    1543
ly  Gly Leu Ser Pro Ser Ile Asp Thr Leu Asp His Ile Arg Ala Leu
     170                 175                 180 gat cgc cta caa gaa gtt ccc cat gag ggt cca atg tgt gac ttg ctg    1591
sp  Arg Leu Gln Glu Val Pro His Glu Gly Pro Met Cys Asp Leu Leu
185                 190                 195 tgg tca gat cca gat gac cgt ggt ggt tgg ggt ata tct cct cga gga    1639
rp  Ser Asp Pro Asp Asp Arg Gly Gly Trp Gly Ile Ser Pro Arg Gly
00              205                 210                 215 gct ggt tac acc ttt ggg caa gat att tct gag aca ttt aat cat gcc    1687
la  Gly Tyr Thr Phe Gly Gln Asp Ile Ser Glu Thr Phe Asn His Ala
             220                 225                 230 aat ggc ctc acg ttg gtg tct aga gct cac cag cta gtg atg gag gga    1735
sn  Gly Leu Thr Leu Val Ser Arg Ala His Gln Leu Val Met Glu Gly
         235                 240                 245 tat aac tgg tgc cat gac cgg aat gta gta acg att ttc agt gct cca    1783
yr  Asn Trp Cys His Asp Arg Asn Val Val Thr Ile Phe Ser Ala Pro
     250                 255                 260 aac tat tgt tat cgt tgt ggt aac caa gct gca atc atg gaa ctt gac    1831
sn  Tyr Cys Tyr Arg Cys Gly Asn Gln Ala Ala Ile Met Glu Leu Asp
265                 270                 275 gat act cta aaa tac tct ttc ttg cag ttt gac cca gca cct cgt aga    1879
sp  Thr Leu Lys Tyr Ser Phe Leu Gln Phe Asp Pro Ala Pro Arg Arg
80              285                 290                 295 ggc gag cca cat gtt act cgt cgt acc cca gac tac ttc ctg taa       1924
ly  Glu Pro His Val Thr Arg Arg Thr Pro Asp Tyr Phe Leu
             300                 305                 310 tgaaatttta aacttgtaca gtattgccat gaaccatata tcgacctaat ggaaatggga   1984
```

```
agagcaacag taactccaaa gtgtcagaaa atagttaaca ttcaaaaaac ttgttttcac    2044
atggaccaaa agatgtgcca tataaaaata caaagcctct tgtcatcaac agccgtgacc    2104
actttagaat gaaccagttc attgcatgct gaagcgacat tgttggtcaa gaaaccagtt    2164
tctggcatag cgctatttgt agttactttt gctttctctg agagactgca gataataaga    2224
tgtaaacatt aacacctcgt gaatacaatt taacttccat ttagctatag ctttactcag    2284
catgactgta gataaggata gcagcaaaca atcattggag cttaatgaac attttttaaaa   2344 ataattacca aggcctccct tctacttgtg agttttgaaa ttgttctttt tattttcagg    2404
gataccgttt aatttaatta tatgatttgt ctgcactcag tttattccct actcaaatct    2464
cagccccatg ttgttctttg ttattgtcag aacctggtga gttgttttga acagaactgt    2524
tttttcccct tcctgtaaga cgatgtgact gcacaagagc actgcagtgt ttttcataat    2584
aaacttgtga actaagaact gagaaggtca aatttttaatt gtatcaatgg gcaagactgg   2644
tgctgtttat taaaaaagtt aaatcaattg agtaaatttt agaatttgta gacttgtagg    2704
taaaataaaa atcaagggca ctacataacc tctctggtaa ctccttgaca ttcttcagat    2764
taacttcagg atttatttgt atttcacata ttacaatttg tcacattgtt ggtgtgcact    2824
ttgtgggttc ttcctgcata ttaacttgtt tgtaagaaag gaaatctgtg ctgcttcagt    2884
aagacttaat tgtaaaacca tataacttga gatttaagtc tttgggttgt gttttaataa    2944
aacagcatgt tttcaggtag ag                                             2966

<210> SEQ ID NO 4
<211> LENGTH: 25
<212> TYPE: DNA
<213> ORGANISM: Artificial Sequence
<220> FEATURE:
<223> OTHER INFORMATION: PCR Primer

<400> SEQUENCE: 4
cactggatca tatcagagca cttga                                            25

<210> SEQ ID NO 5
<211> LENGTH: 21
<212> TYPE: DNA
<213> ORGANISM: Artificial Sequence
<220> FEATURE:
<223> OTHER INFORMATION: PCR Primer

<400> SEQUENCE: 5
ccacagcaag tcacacattg g                                                21

<210> SEQ ID NO 6
<211> LENGTH: 26
<212> TYPE: DNA
<213> ORGANISM: Artificial Sequence
<220> FEATURE:
<223> OTHER INFORMATION: PCR Probe

<400> SEQUENCE: 6
cgcctacaag aagttcccca tgaggg                                           26

<210> SEQ ID NO 7
<211> LENGTH: 19
<212> TYPE: DNA
<213> ORGANISM: Artificial Sequence
<220> FEATURE:
<223> OTHER INFORMATION: PCR Primer
```

-continued

```
<400> SEQUENCE: 7
gaaggtgaag gtcggagtc                                                      19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                     20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                     20

<210> SEQ ID NO 10
<211> LENGTH: 1781
<212> TYPE: DNA
<213> ORGANISM: Mus musculus
<220> FEATURE:
<221> NAME/KEY: CDS
<222> LOCATION: (196)...(1125)

<400> SEQUENCE: 10
cgagcggagg aggaggcaca gcggccggcg gccgagcact gcggagcgag ccagcgggcc         60
ggcgccagcg cccagcagcc gcctggggcc gcagaaagca ccccgggaga cggcggcggc        120
gtgtgcgtgt ggcccgggtg cgggcggcgg cgcgggaaca tcgcggaacg gcagccggtt        180
cgggcgggcg gcatc atg gac gag aag ttg ttc acc aag gag ctg gac cag        231
                 Met Asp Glu Lys Leu Phe Thr Lys Glu Leu Asp Gln
                  1               5                  10 tgg atc gag cag ctg aac gag tgc aag cag ctc tcc gag tcc cag gtc         279
Trp Ile Glu Gln Leu Asn Glu Cys Lys Gln Leu Ser Glu Ser Gln Val
        15                  20                  25 aag agc ccc tgc gag aag gct aaa gaa atc ctg aca aaa gaa tcc aac         327
Lys Ser Pro Cys Glu Lys Ala Lys Glu Ile Leu Thr Lys Glu Ser Asn
    30                  35                  40 gtt caa gag gtt cga tgt cca gtc act gtg tgt gga gat gta cat ggg         375
Val Gln Glu Val Arg Cys Pro Val Thr Val Cys Gly Asp Val His Gly
45                  50                  55                  60 caa ttt cat gat ctc atg gaa ctc ttt aga att ggt gtt aaa tca cca         423
Gln Phe His Asp Leu Met Glu Leu Phe Arg Ile Gly Val Lys Ser Pro
                65                  70                  75 gat aca aat tac ctg ttt atg gga gac tat gtg gac aga gga tat tac         471
Asp Thr Asn Tyr Leu Phe Met Gly Asp Tyr Val Asp Arg Gly Tyr Tyr
            80                  85                  90 tct gtt gaa aca gtt aca ctg ctt gta gct ctt aag gtt cgt tac cga         519
Ser Val Glu Thr Val Thr Leu Leu Val Ala Leu Lys Val Arg Tyr Arg
        95                  100                 105 gag cgc atc acc ata ctc cga ggg aat cac gag agc aga cag atc aca         567
Glu Arg Ile Thr Ile Leu Arg Gly Asn His Glu Ser Arg Gln Ile Thr
    110                 115                 120 cag gtt tat ggg ttc tac gac gag tgt tta agg aaa tac gga aat gca         615
Gln Val Tyr Gly Phe Tyr Asp Glu Cys Leu Arg Lys Tyr Gly Asn Ala
```

|  |  |  |  |  |  |  |  |  |  |  |  |  |  |  |  |
|---|---|---|---|---|---|---|---|---|---|---|---|---|---|---|---|
| | | 125 | | | | 130 | | | | 135 | | | | 140 | |

| aat | gtt | tgg | aaa | tac | ttc | aca | gac | ctt | ttt | gac | tat | ctt | cct | ctc | act | 663 |
|---|---|---|---|---|---|---|---|---|---|---|---|---|---|---|---|---|
| Asn | Val | Trp | Lys | Tyr | Phe | Thr | Asp | Leu | Phe | Asp | Tyr | Leu | Pro | Leu | Thr | |
| | | | 145 | | | | | 150 | | | | | 155 | | | |

| gcc | ttg | gtg | gat | ggg | cag | atc | ttc | tgt | cta | cac | ggt | ggt | ctg | tca | cca | 711 |
|---|---|---|---|---|---|---|---|---|---|---|---|---|---|---|---|---|
| Ala | Leu | Val | Asp | Gly | Gln | Ile | Phe | Cys | Leu | His | Gly | Gly | Leu | Ser | Pro | |
| | | | 160 | | | | | 165 | | | | | 170 | | | |

| tcc | ata | gac | aca | ctg | gat | cac | atc | cga | gca | ctc | gat | cgc | cta | cag | gaa | 759 |
|---|---|---|---|---|---|---|---|---|---|---|---|---|---|---|---|---|
| Ser | Ile | Asp | Thr | Leu | Asp | His | Ile | Arg | Ala | Leu | Asp | Arg | Leu | Gln | Glu | |
| | | 175 | | | | | 180 | | | | | 185 | | | | |

| gtt | cct | cat | gag | ggt | cca | atg | tgt | gac | ttg | ctg | tgg | tca | gat | cca | gat | 807 |
|---|---|---|---|---|---|---|---|---|---|---|---|---|---|---|---|---|
| Val | Pro | His | Glu | Gly | Pro | Met | Cys | Asp | Leu | Leu | Trp | Ser | Asp | Pro | Asp | |
| | | 190 | | | | | 195 | | | | | 200 | | | | |

| gac | cgt | ggt | ggc | tgg | ggg | ata | tct | cct | cgg | gga | gct | ggt | tat | acc | ttt | 855 |
|---|---|---|---|---|---|---|---|---|---|---|---|---|---|---|---|---|
| Asp | Arg | Gly | Gly | Trp | Gly | Ile | Ser | Pro | Arg | Gly | Ala | Gly | Tyr | Thr | Phe | |
| 205 | | | | | 210 | | | | | 215 | | | | | 220 | |

| ggc | caa | gat | att | tct | gag | aca | ttt | aat | cat | gcc | aat | ggc | ctc | acg | ttg | 903 |
|---|---|---|---|---|---|---|---|---|---|---|---|---|---|---|---|---|
| Gly | Gln | Asp | Ile | Ser | Glu | Thr | Phe | Asn | His | Ala | Asn | Gly | Leu | Thr | Leu | |
| | | | | 225 | | | | | 230 | | | | | 235 | | |

| gtg | tcc | aga | gct | cac | cag | ctg | gtg | atg | gag | gga | tat | aac | tgg | tgc | cat | 951 |
|---|---|---|---|---|---|---|---|---|---|---|---|---|---|---|---|---|
| Val | Ser | Arg | Ala | His | Gln | Leu | Val | Met | Glu | Gly | Tyr | Asn | Trp | Cys | His | |
| | | | 240 | | | | | 245 | | | | | 250 | | | |

| gac | cgg | aac | gta | gta | aca | att | ttc | agt | gct | cca | aac | tat | tgc | tat | cgt | 999 |
|---|---|---|---|---|---|---|---|---|---|---|---|---|---|---|---|---|
| Asp | Arg | Asn | Val | Val | Thr | Ile | Phe | Ser | Ala | Pro | Asn | Tyr | Cys | Tyr | Arg | |
| | | 255 | | | | | 260 | | | | | 265 | | | | |

| tgt | ggt | aac | caa | gct | gca | atc | atg | gaa | ctt | gac | gac | act | ctt | aag | tat | 1047 |
|---|---|---|---|---|---|---|---|---|---|---|---|---|---|---|---|---|
| Cys | Gly | Asn | Gln | Ala | Ala | Ile | Met | Glu | Leu | Asp | Asp | Thr | Leu | Lys | Tyr | |
| | | 270 | | | | | 275 | | | | | 280 | | | | |

| tct | ttc | ttg | cag | ttt | gac | cca | gca | cct | cgt | aga | ggc | gag | cca | cat | gtc | 1095 |
|---|---|---|---|---|---|---|---|---|---|---|---|---|---|---|---|---|
| Ser | Phe | Leu | Gln | Phe | Asp | Pro | Ala | Pro | Arg | Arg | Gly | Glu | Pro | His | Val | |
| 285 | | | | | 290 | | | | | 295 | | | | | 300 | |

| act | cgt | cgt | acc | cca | gac | tac | ttc | ctg | taa | tgaaaatgta | aacttgtaca | 1145 |
|---|---|---|---|---|---|---|---|---|---|---|---|---|
| Thr | Arg | Arg | Thr | Pro | Asp | Tyr | Phe | Leu | | | | |
| | | | 305 | | | | | 310 | | | | | gtattgccat gaaccgtata ttgacctaat ggaaatggga agagcaacag taactccaaa    1205 gtgtcagaaa atagttaaca ttcaaaaact tgttttcaca cggaccaaaa gatgtgccat    1265 ataaaataca aagcctcttg tcatcaacag ccgtgaccac tttagaatga accagttcat    1325 tgcatgctga cgcgacattg ttggtcaaga atccagtttc tggcatagcg ctatttgtag    1385 ttacttttgc tttcttgaga gactgcagat ataggattaa acattaacac ccgtgagtcc    1445 agttgacttc acttagctgt agcttactca gcatgactgt agatgaggat agcaaacaat    1505 cattggagct taatgaacat ttttaaataa gtaccaaggc ctcccctctt gttgtgtttc    1565 tttcagggat accattaatt taattgtatg atttgtctgc actcagtttc tccccttctc    1625 aaatctcagc cccgcgttgt tctttgttac tgtcagaaaa cctggtgagt tgttttgaac    1685 agaactgttt ccctcctgta agatgatgtt actgcacaag tcaccgcagt gttttcataa    1745 taaacttgag aactgagaaa aaaaaaaaa aaaaaa    1781

<210> SEQ ID NO 11
<211> LENGTH: 22
<212> TYPE: DNA
<213> ORGANISM: Artificial Sequence
<220> FEATURE:
<223> OTHER INFORMATION: PCR Primer

<400> SEQUENCE: 11
tcaacagccg tgaccacttt ag                                              22

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
cgctatgcca gaaactggat tc                                        22

<210> SEQ ID NO 13
<211> LENGTH: 24
<212> TYPE: DNA
<213> ORGANISM: Artificial Sequence
<220> FEATURE:
<223> OTHER INFORMATION: PCR Probe

<400> SEQUENCE: 13
ccagttcatt gcatgctgac gcga                                      24

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                           20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagat                                           20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                   27

<210> SEQ ID NO 17
<211> LENGTH: 2181
<212> TYPE: DNA
<213> ORGANISM: Homo sapiens
<220> FEATURE:
<221> NAME/KEY: CDS
<222> LOCATION: (210)...(1139)

<400> SEQUENCE: 17
agagagccga gctctggagc ctcagcgagc ggaggaggag gcgcagggcc gacggccgag      60
tactgcggtg agagccagcg ggccagcgcc agcctcaaca gccgccagaa gtacacgagg     120
aaccggcggc ggcgtgtgcg tgtaggcccg tgtgcgggcg gcggcgcggg aggagcgcgg     180
agcggcagcc ggctggggcg ggtggcatc atg gac gag aag gtg ttc acc aag      233

```
                          Met Asp Glu Lys Val Phe Thr Lys
                           1               5 gag ctg gac cag tgg atc gag cag ctg aac gag tgc aag cag ctg tcc       281
Glu Leu Asp Gln Trp Ile Glu Gln Leu Asn Glu Cys Lys Gln Leu Ser
    10              15                  20 gag tcc cag gtc aag agc ctc tgc gag aag gct aaa gaa atc ctg aca       329
Glu Ser Gln Val Lys Ser Leu Cys Glu Lys Ala Lys Glu Ile Leu Thr
 25              30                  35                  40 aaa gaa tcc aac gtg caa gag gtt cga tgt cca gtt act gtc tgt gga       377
Lys Glu Ser Asn Val Gln Glu Val Arg Cys Pro Val Thr Val Cys Gly
             45                  50                  55 gat gtg cat ggg caa ttt cat gat ctc atg gaa ctg ttt aga att ggt       425
Asp Val His Gly Gln Phe His Asp Leu Met Glu Leu Phe Arg Ile Gly
         60                  65                  70 ggc aaa tca cca gat aca aat tac ttg ttt atg gga gat tat gtt gac       473
Gly Lys Ser Pro Asp Thr Asn Tyr Leu Phe Met Gly Asp Tyr Val Asp
     75                  80                  85 aga gga tat tat tca gtt gaa aca gtt aca ctg ctt gta gct ctt aag       521
Arg Gly Tyr Tyr Ser Val Glu Thr Val Thr Leu Leu Val Ala Leu Lys
 90                  95                 100 gtt cgt tac cgt gaa cgc atc acc att ctt cga ggg aat cat gag agc       569
Val Arg Tyr Arg Glu Arg Ile Thr Ile Leu Arg Gly Asn His Glu Ser
105             110                 115                 120 aga cag atc aca caa gtt tat ggt ttc tat gat gaa tgt tta aga aaa       617
Arg Gln Ile Thr Gln Val Tyr Gly Phe Tyr Asp Glu Cys Leu Arg Lys
            125                 130                 135 tat gga aat gca aat gtt tgg aaa tat ttt aca gat ctt ttt gac tat       665
Tyr Gly Asn Ala Asn Val Trp Lys Tyr Phe Thr Asp Leu Phe Asp Tyr
        140                 145                 150 ctt cct ctc act gcc ttg gtg gat ggg cag atc ttc tgt cta cat ggt       713
Leu Pro Leu Thr Ala Leu Val Asp Gly Gln Ile Phe Cys Leu His Gly
            155                 160                 165 ggt ctc tcg cca tct ata gat aca ctg gat cat atc aga gca ctt gat       761
Gly Leu Ser Pro Ser Ile Asp Thr Leu Asp His Ile Arg Ala Leu Asp
        170                 175                 180 cgc cta caa gaa gtt ccc cat gag ggt cca atg tgt gac ttg ctg tgg       809
Arg Leu Gln Glu Val Pro His Glu Gly Pro Met Cys Asp Leu Leu Trp
185                 190                 195                 200 tca gat cca gat gac cgt ggt ggt tgg ggt ata tct cct cga gga gct       857
Ser Asp Pro Asp Asp Arg Gly Gly Trp Gly Ile Ser Pro Arg Gly Ala
            205                 210                 215 ggt tac acc ttt ggg caa gat att tct gag aca ttt aat cat gcc aat       905
Gly Tyr Thr Phe Gly Gln Asp Ile Ser Glu Thr Phe Asn His Ala Asn
            220                 225                 230 ggc ctc acg ttg gtg tct aga gct cac cag cta gtg atg gag gga tat       953
Gly Leu Thr Leu Val Ser Arg Ala His Gln Leu Val Met Glu Gly Tyr
        235                 240                 245 aac tgg tgc cat gac cgg aat gta gta acg att ttc agt gct cca aac      1001
Asn Trp Cys His Asp Arg Asn Val Val Thr Ile Phe Ser Ala Pro Asn
    250                 255                 260 tat tgt tat cgt tgt ggt aac caa gct gca atc atg gaa ctt gac gat      1049
Tyr Cys Tyr Arg Cys Gly Asn Gln Ala Ala Ile Met Glu Leu Asp Asp
265                 270                 275                 280 act cta aaa tac tct ttc ttg cag ttt gac cca gca cct cgt aga ggc      1097
Thr Leu Lys Tyr Ser Phe Leu Gln Phe Asp Pro Ala Pro Arg Arg Gly
            285                 290                 295 gag cca cat gtt act cgt cgt acc cca gac tac ttc ctg taa tgaaattta   1149
Glu Pro His Val Thr Arg Arg Thr Pro Asp Tyr Phe Leu
        300                 305                 310
```

-continued

```
aacttgtaca gtattgccat gaaccatata tcgacctaat ggaaatggga agagcaacag    1209
taactccaaa gtgtcagaaa atagttaaca ttcaaaaaac ttgttttcac atggaccaaa    1269
agatgtgcca tataaaaata caaagcctct tgtcatcaac agccgtgacc actttagaat    1329
gaaccagttc attgcatgct gaagcgacat tgttggtcaa gaaaccagtt ctggcatag     1389 cgctatttgt agttactttt gctttctctg agagactgca gataataaga tgtaaacatt    1449
aacacctcgt gaatacaatt taacttccat ttagctatag ctttactcag catgactgta    1509
gataaggata gcagcaaaca atcattggag cttaatgaac attttttaaaa ataattacca   1569 aggcctccct tctacttgtg agttttgaaa ttgttctttt tattttcagg gataccgttt    1629
aatttaatta tatgatttgt ctgcactcag tttattccct actcaaatct cagccccatg    1689
ttgttctttg ttattgtcag aacctggtga gttgttttga acagaactgt ttttcccct    1749 tcctgtaaga cgatgtgact gcacaagagc actgcagtgt ttttcataat aaacttgtga    1809
actaagaact gagaaggtca aatttaatt gtatcaatgg gcaagactgg tgctgtttat    1869 taaaaagtt aaatcaattg agtaaatttt agaatttgta gacttgtagg taaaataaaa    1929
atcaagggca ctacataacc tctctggtaa ctccttgaca ttcttcagat taacttcagg    1989 atttattgt atttcacata ttacaatttg tcacattgtt ggtgtgcact ttgtgggttc    2049
ttcctgcata ttaacttgtt tgtaagaaag gaaatctgtg ctgcttcagt aagacttaat    2109
tgtaaaacca tataacttga gatttaagtc tttgggttgt gttttaataa aacagcatgt    2169
tttcaggtag ag                                                       2181
```

<210> SEQ ID NO 18
<211> LENGTH: 40000
<212> TYPE: DNA
<213> ORGANISM: Homo sapiens
<220> FEATURE:

<400> SEQUENCE: 18

```
ggccttgcca aacacgttgt cttggataaa ggaggatttt cagtcctgct attggctgat      60
ggggcctcca gtgccttctt cagcctgttg gtggggatga tgccctcaga gccgcagagt     120
gagcagtctc ctcccaagca tcgctgagca cttgggtgtg gaagggttgc ctgatactga    180
gggtggggtt cctggaagac aggcgatcag gttcagctct tgccttgccc tttatggtta    240
aatgttcttt ggaaagcttc tatatctttc aaatcctggg ggcattatga tctctcttct    300
gcctatccca aaccatcttc agccagtact gttgggagaa tacaagctcc agggcatggt    360
ccctggtccg tctggatgac ccctccggat ctggcatata gctggcgctc tatggaacca    420
gatatttatg taaaagcagg gacaatggaa tgtgaaaacg tttcgcaaac tccaaagcga    480
ttcataacca gacagaggtc caatcctagg gtatacgagc tctctctttt aagcacgtat    540
cacagctgct tctcacgcca ccgagacgcg gtcaggacag gtgcatccat cttctctggg    600
cttcccctct tgaaagtagg ccagggcgcg caggggttga gggtctctca ttcccagaga    660
gaattaaact tggaggaaag caaccaccgg cgaggagcgg ggcgcgtgga agcgagccgc    720
ggtccgaggc ccaaagaaaa gcccaagcct cgccccgcc atcgcgcccg acgagacacc     780
taggtccggg gacgggtgtg tgccgcgaa gtcaggtgca ctgcgcagca ctccccggt     840 aggtacacgc tcctccacct acgagtgacc taattacaag gtgccagccg cgcccagagg    900
tgggggtggt taatccaagc ggccactcgc tgccgttcc tgcccccaaa gatgacggaa     960
acccacacga ttacagagcc gcagcacccc agatgagcca cggggtcgca attctcgttt   1020
```

-continued

```
ccgtgatcgg actgccaggc cccaggtgag gagctgagtt catcaccaga gcggccttcc    1080
cagggggaacc agttacaggc tgccagtggc cccggcttcc atccggtctg cgcctgcgcg   1140
cggcccaagc cctcgcctct cctggaatag tgctcaggga ttagtccggt tcgccgctgt    1200
gcgcactgcg catgctccag ctccatcctt cccttccccc accacccgc cctccgggag     1260
ccacgcccaa aaagtcaagg cgcttcagtt accagccggc tacgtcgcgc ctgcgctttg    1320
accccccagtt tgcgccccaa ctccggtcgt gcggccgccc ggggagggct ctgcagttgc   1380
gcagcttgct ccccggccct ttccccctcc gctccccgcc gcctcctgac gccgggcgtg    1440
acgtcaccac gcccggcggg cgccattaca gagagccgag ctctggagcc tcagcgagcg    1500
gaggaggagg cgcagcggcc gacggccgag tactgcggtg agagccagcg ggccagcgcc    1560
agcctcaaca gccgccagaa gtacacgagg aaccggcggc ggcgtgtgcg tgtaggcccg    1620
tgtgcgggcg gcgcgcggg aggagcgcgg agcggcagcc ggctggggcg ggtggcatca     1680
tggacgagaa ggtgttcacc aaggagctgg accagtggat cgagcagctg aacgagtgca    1740
agcagctgtc cgagtcccag gtcaagagcc tctgcgagaa ggtgagctgt agtacggctg    1800
cggacagccg ccgcggggcc gagcccgccg aggaaaaggc ggccgtgagg agggtgcaac    1860
atggcggagg ccgccggtcc gggccccccg agtctccgag accggcgccc atcctggccg    1920
gcggcggctt cctaacgacc cggcgccccc tgcctcccgc gcaggattg gttgccgccg     1980
ccgcctaaaa tggcgccgtt cactcgactc ctgggctttt gagtcagccg gccttggcgc    2040
cagacgaggt ggcaggggga gcggagaccc tgtgggtcat cgtcagggac ggttttgagg    2100
gtgagctggc ttggattctg cggcttggga atggagcctg ggcctctccg gtgggctgag    2160
taagagtctt tccgctggta cccaggccta gttaggtcca gagctgccca gaggatcccc    2220
caaaggcagt cttgttaggc cgtatcccag aacatacta aaggtcacac agctttagta     2280
cccccttggtg gtttgtatta tactcaccaa gcgatcttct ccagaaatca aggtaagggg   2340
tgtcttttaag aatttttaaa ttattctctt aacctaattt ttacgaaggt catggtggta   2400
gctataaggg aggagtgtaa cttatttttc atagttggaa gaaatcggga atttggtgag    2460
tcatactaca taaggagctt ttggattgga aatcaagtgt cggttgaata tgatttatat    2520
gctgactcaa agccttctct aagcttaaca cacttggcat tttgccgttt atttttaaaa    2580
tgaaccacat aaaatggaag agcggtaaat tttgtatctt tgttgcaaaa attacttgat    2640
agtattttgt ggctgcaagt agtagtagtg ataataactg tcgactgaga ttgtattcca    2700
gacattgtgc ttagtgttta ataatgtct cacatacact gaaaatagaa tgttgtagtc     2760
cacttagtaa cactaaactt tatattagct aattcccttt tgttttcccc tggggggttgg   2820
ggaaacaggt agttaattta gctattagct ttgtgttgta tttttaaatt cttgtaactc    2880
agttttctaa agtacacaaa atgctgatct ctgctgtgaa catttttaact tcccttttca   2940
aaattaactt tgcagcacgt cactttagta cagaatagtg gagtatcata ttagcatttt    3000
gtatccgtga aaagaattaa tggagaacta ttatcctgat ttgtttctgg tttgatgtga    3060
aaattaggtt catgagtttg acgtatatgt ttccaagaca ggcttttttta gaaaccatgt   3120
tgtgaacaat tggaatttaa gtaagtcaga tttagatttg tttctcccaa gcctgaacaa    3180
aactactact agtggatgag gtggcacatc atctgttgga gatgcttttt aatggtagcg    3240
atgtattgaa tctcctgttt ctttacccctc tcacgtcaaa tgaggttggt atttattta    3300
aaggtttaaa attggccttt aaaaatgaat gtatattgcc aggtcttaat ttctaggtac    3360
tgtacatgat gatcttaccg atttttggaa ttcagtgcat tatatgaaag acttttaagt   3420
```

```
cagtagttgg ccagttgact agtcttttga agaaaacgtg gaaaggaggg aggtgatgac    3480
gtaactggaa gactggactg cgagttagat ttggacatga gtccttctgc tcttccttga    3540
gtaattgtga cagactttgg gacagccact tcacttgtcc ttgttttcct gtctataaac    3600
taaaatgtgt tctgagatta tacagtcaat tccgttttaa attagtagtg tgtttaatat    3660
tgaacatcta ttgaatatct aagattgcat actcttttga gggaaatgaa aagcaatgaa    3720
gaataagtat gcttattgtc gaggagctat gaatctagtt tgaaagaaaa gcatggtatg    3780
aaaaggtgtg ggagatggag catggaagta gagggtttgt gttggaaact gttgtagaag    3840
ataagataat actggatgct agagtggggt gggtgaagct gatgcatcta atattgcttt    3900
ccacatcttt gtaaaactaa gatgtagtga ggtaaatctc cattgcttgc gctgcttacg    3960
caaattttag ttctgagtgc caaaaagat ggaaataata tttgagagta ggtgttacat     4020
aaaagtttct gtggaatgga tccgttttgg tggatatcat tatacaacct tcatactgtt    4080
tataactggt aagtaagtat ttcaactttc aggatgatat taaacttcca aactaaatta    4140
atttgaagac agttttttgg gtatgtagaa tccatgaact gatgtttttt gtacaagtct    4200
ttctagtaaa acaaaagctg tctttcactg ttaatatttg tgtgccaatg gcatctctgg    4260
gtgaaagcta catatgtgct ttttggtgtg attgccttct aaagagtaat tttgaaaatt    4320
tgagggctaa ttttttttcat tagtgtataa taatagtatt ttttgagaaa aagatactt    4380 gttaatagtt gataatttct tcaatcataa gaaggaatga taatgtaaaa gccttccttc    4440
tacccaccta aatgcctgat ttgaagggga aatatttaaa tagtaaaaat agatgtatac    4500
cataagaggt cattgttact aaaaaatcct gaggccattt ttttgttatc ccatcaacaa    4560
ttaacagtgt tacatgttca gaactgagag aatctaagta tgcatttata aaagacaaga    4620
gtgaacatgg tttttatgtt actgactagc taaaaagaat tttaagatgt gattaagact    4680
tatacaaaag ccaaggttgt tagtgtatag tatactttgt catcttgaga atcataattt    4740
gttgatagtt taataatttg gtgtgcagct ttgcctcagg ctcagttcta taatcagcat    4800
tacatcagta taactggccg ggtatgtttc aatctacaga ttgaaaggag taaatagtat    4860
caacttgctt ttgcattgac tacagtaaac aatcttttat tatgtgactt cagctttgtt    4920
ttagcttggg tatgatttct tggctttgtg cttaccaaac atgtggagaa cgttgtttga    4980
tagccagatt tttttttttc aaagaagttc tttacctagg tatgctgttt tccattgctt    5040
tgcaagcact ataaataaag tgcagtcatt agtcattaaa atgttagttt taacatttgt    5100
tacgtgagta tggaaaaaac aaactgcttc cttctaatta gatgagctga aaatatttg     5160 accaagatga cattcttgta tgaattgggt aatatgttgc tgtgagtatg tgtgtacgtt    5220 tcatttttaaa gggtgtttgg ctcatttctc tagaagtgat ttgaatattg aggacaagca    5280
ggtgggggaa gcatgttaca gaacattatt tttatcatac ttttataaga tattgttctc    5340
agttacagat gcaacccaaa gactcagaaa ggtaaagtga cttgactaaa ggggctaaaa    5400
gtgagattgc caaggcttgt ggattctaag cctaatgttc tggtattgct tcacagatcc    5460
ccttctgttt tcagaggtag tgttagtagt gaaagatgta ggtaaattgg ggccaagcta    5520
aattgggaag tcaacacttt cataaaataa aactttttt tttttttttt tttgagataa     5580
ggtcttactc ttttgcccag tctggagtgc agtggcgcaa tctcggctca ctgcaacctc    5640
cacctcccag gttcaagcag ttctcctgca tcagtctccc tagtagctgg gattacaggt    5700
acccaccacc atgcccagct gttttgtatt tttagtagag atgggatttc accatgttgg    5760
```

-continued

```
ccaggctagt ctcgaactcc tgaccttcag tgatccaccc acctcagcct cccaaagtgc    5820
tgggattaca ggcttgagcc agcgcgcctg gccaaaacat tattttatt ttcattgctt    5880
gaaagcttcc tattcatgtt acatactgtt gttccgcttt gtcttggaaa gagtaattat    5940
tattcagttt tggatgtagc tgacaacatt tgcccctcaa atgagattgg tgagatgaaa    6000
accctagata atttcccttg tattcttagt ataaatcatg atccagagac tgagctctaa    6060
agtattctaa taaagtataa ctgactttt atattgttta ttgcaactta taaaatgcct    6120
cttttcagca gggcaaggtg gctcacacgc ctgtaatcct agcactttgg aaggccacgg    6180
caggcggatc accaggtcag gagaccaaga ccaatcctgg ctaacacggt gaagcccgt    6240
ctctacttaa aaatacaaaa aattagccgg gcgtggtggc acacacctgt agtctcagct    6300
actgggagg ctgagacagg agaattgctt gaacctggga ggcggaggtt gcagtgaacc    6360
aagattgtgc cactgcactc cagcctgggc gacagaggga gaccccattc cccccggccc    6420
caaaaaagcc tcttttcatc ctcttggctt ccacagtcaa atgtcatgca tgtgtgtatt    6480
tgtttcatgg tctcctaggc aggaagctgt aatgcagtta gtttggagtt gacttcatga    6540
ggaaacagaa aaggtgaaca ttcccactat tcagaaacac aggttcccca accctcccta    6600
cgttctccac tgggaccaga attgtatgtt ttcagaaaat tggctgtaag gctaagttga    6660
agctcatgta ctgtagaaag aatgaaggac ccttcaggag tatgtggat aacatttgta    6720
ttaccagtct ggtgtggccc tgttttatgg cagcaaatat gttccctatc tcatggtaag    6780
tcaggtttgt cagagttacc tgtgagatag cctttgctta gtttggaagg ggtaagttag    6840
gaaaactaag agactgggtt tggtgggtc ttttatcagg gtactgagga gagaggcaaa    6900
gctatatgta acagggagac actatttatt ctttctgctt tgacccattt ctcttacttc    6960
attatcatcc ttgcctgaga aagctgtcaa cctccactca tacacaggca gatctgaatt    7020
ggatgagaac catgaaggag gaagattttt gttttgtgg gctttttttt ttttttttt    7080
tttttttttt gagatagagt ctcacagtcg cccaggctgg agtgcagtgg tgtgatctcg    7140
gctcactgca ccctctgcct cccaagttca agcagttctc ctgcctcagc ctcccaaata    7200
gttgggatta taggtgtgtg ccaccacacc cagctaattt ttgtatttt agtagagaca    7260
gggtttcacc atgttggcca ggctggtctt gaactcctta cgtcaagtga tccacccatc    7320
tcagcctccc aaagtgctag gattacaggc atgagccact ggcaccagac ctgttttgt    7380
tttaaataga ttttctttg gcttctgggg cagaagtggt agaccaggct gaagaaggga    7440
gaggtgtcta ttgtcagtaa atggctgaga ggtggggttt gaaagaatgg taagaacaa    7500
cctgagatta actgcttttt tttttttttt ttttgatacg gagcctcgct ctgttgccca    7560
ggccagagta cagttgcatg atctcggctc actgcaacct tgtctccca cgttcaagtg    7620
tttctcctgc ctcagcctcc tgagtagctg ggattacagg catgtgccac catgcctagc    7680
taattttttt attttagta gagacagggt ttcatcatgt tggccaggct ggtcttgaac    7740
tgctgacctc aagtgatccg cccgcctcag cctcccaaag tgctgggatt acaggtgtga    7800
gccactgtgc ccagctaact gcttaacttc ttcacattgc agtattattg cctgtttatt    7860
ggtctgttgt ggattgtggt ttagaatgga tgaacaaggc agtgacacag atgcgtgtat    7920
atctgaatct gggtattttt taaactaaat gtgaccagtt ggccagtccc tcttgcaccc    7980
tgtgttgcca cttctgcctt agtttagtca tttagttgct actacagatg gggatttta    8040
ccctgctggt gttgaggctg gaaggttgca aacctttgtc ctagatgggg acgaggagta    8100
gaatgggaga caagcagtag catgtgttta cctggccaaa ggcctgcaaa atgtagttca    8160
```

-continued

```
cagaggttat ggagtgtcat tgatgctatc gtgtgacagt gtacatttga ttttggaacc      8220
agtatttaat aaaccttcat tgtatgcatt attgtcacta ttgagctttg tctaaaaagc      8280
actaccttat tctcgtgtat aaggatttct tagtttggtt ttgctctaat taatagcaca      8340
gttttggatt agtcaggaga ttgactttat agttaattct agatagggaa tgttttagaa      8400
tgcttgtgcc ggtggtgatc aagtaactta tttttctgcc actaatctgt aaatgagcaa      8460
taatgcccac tatctatttc ttttggctgg ctttacttaa taaataggc ttaagacatg       8520 ctttaggatg gggtagaatt ctagtaatgg aatcaacctt aaagaccatc taggctggcg      8580
gggcacagtg gctcacgcct ggaatcccag cactttggga ggctgaggtg ggtggatcac      8640
gaggtcagga gatggagccc atcctggcta gcacggtgaa accccgtctc tactaaaaat      8700
acaaaaaatt tagccaggca tggtggtggg cgcctgtagt cccagctgct cgggaggctg      8760
aggcaggaga attgcttgaa cccagcaggc agaggttgca gtgagccgag atcgtgcccc      8820
tgcactccag cctaagcgac agcaagactc catcttaaaa gaaaaaaaaa aaaaagaaa       8880 gaaacaacca tctagactaa ttcatcttac acagatgagg gaggaaactg agacccagag      8940
tggttgaatc ttgttcatga tgtattattg tgacaatttt ttaataagta gatatatagc      9000
agcatttctc agttgtgtag tagattaaaa cttcttttc tatgcaggaa tgattgggag       9060
tgtttaattc attcacatat gtaggttagt tggtaaaggt tgagtttagt ctattgtgca      9120
tatgagacat agggctttaa ggatctttcc ttttggtcag aggcaaaggt gatattgcag      9180
aaacagatgg gaaaactcac aaattttata ttttctttta ttacactttt agaattatcc      9240
ctcattccca acatttttct tttatttagg tcctaagcct tagagccaaa cagaaaatac      9300
tagttactag aatattacct ggagggttaa acttttaaaa tataaccata ctgattttaa      9360
tcaaagaaga ttgaaatgtt tcgtgaaata ttagtggtat ctgttcagtg tagttaatga      9420
aagacaagta gtcatgcacc acataatgac attttggtca gtggtggact gcatgtgatg      9480
gtggtcttat gaaattataa tggagctgaa aaattcctat cacctggtga ccttgtaatg      9540
tcatagtgta acactttata ttgtttatgt ttagttatac aaatacttaa cattatgtta      9600
acagttgcct acagcattca gtacagtaaa tgctgtacaa gtttgtagcc taggagcaat      9660
aggctatcca atagcttagg tttgtagtag tctatactat ctagatttgt gtaagaccac      9720
tctgtgatgt tcacacaaca actaaataat ttgatgtatc cctgcgcatta agcaacacat     9780 gattagtatg aagaatggtt tgatagttga aggaaattaa ctcaaaactc atttgcttcc      9840
agggctagta atatgttcta catcatgtat caccccacgc ctcaaactct agccctgtac      9900
actaacttat cacaaacctt ggatttttt gcacaattat caaaatgaca tatcaaacca      9960
accgtacatc ttgacataaa aacagtatga gacaaaatga aattctcttg ggatattgaa      10020 aaaattttt ttgcctgtga atttagtaat tttacttatt aagaatttc aaatgatttc       10080 agttcttaaa ctgaaaaata aaattcaaaa attaattgca ttttttccag tgtttcttct      10140
atgtctttat attggtagaa ctgtccaact atatggtaag gatgtgaaat gttaaattta      10200
cttgaactag agttacaatg aacattagaa ttaataatca gacttctttt tttttctttt     10260
ttttgagaag ggagtttcgc tcttgttgcc caggctggag tgcagtggca cggtcttggc      10320
tcaccgccac ctccaccttc cagattcaag caattctcct gccccagcct cccgggtagc      10380
tgggattaca ggcatgcgcc accacaccca gctaatttt gtattattag agatgggtt       10440 tctctgtgtt ggtcaggctg gtcctcaaac tcccgatctc aggtgatctg cctgccttgg      10500
```

-continued

```
cctcccaaag tgctgggatt acaggcgtga gccacttcgc ccggccaata atcgagacttt    10560 tagtagtaaa attactttca aaaatggaga ttcctttgtc aaatagtact attattagta    10620
ctaagattgt aaagaggtta tttgtgtctg attttgagtt tgatgctaca gagaagacag    10680
gttaggcctg cattgacgtt tttcatcaag ggcagaattg atgatacaga aacttgattt    10740
ctgtctaggc atggtggctc atacctacaa tcctggtgct ttgggaggcg gaggctggaa    10800
gctcactcga gactaggagt ttgagaccag cttgggcaat gtagtgagac caccgtttct    10860
acaaaacaaa aaacaggttt ctttagttaa gtataaatca ttgatctgtg attaatccaa    10920 acacttttc ctcagtatag accttgggt tcttcggtgt ttgactacct tcttttgaag     10980
gaaaccacct tttttttttt tttttttttt tttgaggcag tctcactctg ttgcccaggc    11040
tggaatgcag tggcacaatc tcagcccact gcaacctccg cctcatgggt tcaagtgatt    11100
ctccagcttc agcctcctga gtagctggca ttacaggcat gcaccaccat gcccagctaa    11160
tttttgtatt tttagtaggg aggggggtgt ttcgccatgt tgcccaggct gttctcaaac    11220
tcctgacctc aagcgatcca cccaccctgg cctcccgaag tgctgggatt acaggcatga    11280
tccaccgtgc ccacccgaaa ccacttgtaa tataccttta ggagaatgct tttagttaca    11340
tcatgatccc tttcatgtag ctaacaacaa aaatgaatat taaccccaaa tattggaact    11400
cgtattttga agcaagttat ttcttggtat actttagtgc cagaattggt actgttatgt    11460
gattaactgt ttttgagact aagaaaatat tttgctggac atctgatgaa attatcttaa    11520
aaacagtgct tgggtgtttt ccctggagtg tagtggcaag agtactctgt tgtccatcag    11580
agccacttgc tgctctcagc tggccttgct gttgaatggc ataatctgat ttcgttggag    11640
tacccaagtc ctaagatttg aagaataagg gttattatct cagtctcatc ttttctctga    11700
gatagcattt gttcaggaaa tgttatctgt tttcaatggt gaagggagtg agagtctgct    11760
taggagttac tgtatacatt aaacattggt gaccggcctt taaagaatta gaggctaggc    11820
ctggtgactt acacctataa tcccagcaga ttgggaggcc agggcaggag gatatcttga    11880
gcccgggagt tcaagaccag cctaggcagc atagtgagac cctgtctcta caacaaaatt    11940
tttacttttt tatttttatt tttatttttt gagatggagt tttgctctgt cacccaggct    12000
ggagtgcagt ggcatgatct tggctcactg caacctccac ctcctgggtt caagcgattc    12060
tcctgcctca gcctcctgag tagctggac cacaggcgag ggctaccatg cccagaatat    12120
ttttgtattt ttttttggt agagatgggg tttcaccact ttggccaggc tggtcttgaa    12180
ctcctgacct caagtgatcc acctgcctcg gcctcccgaa gtgctgggat tacaggcgtg    12240
agccactgca cccagcccta cgaataattt ttaaaaataa attagttggg tgtggtggca    12300
cacctgtggt tctagctact ctgtgaggct gaggcaagag gattgcttgg gtccaggaga    12360
tctagactgc aatgagctgt gatcatgcta cagcactcga agcctgggga acagagcaag    12420
aacttgtctc aaaaaaaaaa aaaaagtaa ataaatatta gacacttctc aagccctagg     12480
tcccaattga ttgatttttt tttttcttgg atgcaggatt ccaaaatact tcaaggtcat    12540
tattaaacat ttaaagttaa tgtcataatg ttaacgatgc aagtttaaga tgctgatata    12600
aaaagaagct tgagtagttg tcgtgtaatc ttaggattaa agtatagatt ttaaaatgaa    12660
aaactcttag aaaatggcaa gacgtgataa cttttcttaa taattgtagg agaaaaatta    12720
caaagcaaaa atgggcatag aaaatttctg gctatatatt taaaaaataa gagaaaatgc    12780
caaaaagtta cttaaaataa cagtttaaaa tagtttatac aaatacttca gaacatcatc    12840
tagctcttaa tgatcagatg ttcaaaaata ttcatggaca acttgtataa gaggagaaat    12900
```

```
aactgatggt aaataaacat ggaataaaaa gtttgtactc agaaatgaaa aatgccaatt   12960
aaattagtga taccacattg tatatctgaa atagctgaga atgagtatat tctttcattt   13020
attattgtat aacaaattgg cataattgag ttttatagta catatgaaac aaaaaaagtt   13080
aatgctattt tgccctgtaa tcccacaatt aaagctttt gaaaggaaat aattcaaatg    13140
agcaataata ctgtacacgt ataggtctat ttagaagggc attatgtagt tttaaaaaat   13200
cactataatg tagaaacgag ttagtatgaa actttaggac acaaaatgag atgccagtca   13260
attataagta agaggtctgt gtgggtaaaa actgaaaggt aatagaaatg agaagaattc   13320
tggttggtaa gaataagata gttatatatc ttaaagcttt cagtgaaatc ttaaccttt    13380 aatttttttt ttagccttt tttgttagtt ttgagagaga gtcttactgt gttgcatagg    13440
ctggagtgca gtggcacgat ctcagctcac tgcaacctct gcctcctggg ttccaataat   13500
tctcatgcca cagcctccca agtagctggg attacaggcc tgtgccatct tacctggctg   13560
atttttgtat ttttagtaga gatggggttt tactgtgttg gccaggctgg tcccaaactc   13620
ttgacctaaa gtcatccacc tgctttggct cccaaagtga tagaattaca ggcgtgagcc   13680
actgtgcctg gcttttcag cctttttta atgcaaagaa ttgtgacatg gttgtaatca     13740
ttttgtgctt ttatttattt attttgagat ggtgttgttg cccaggctga agtacagtga   13800
catcatcata gttcactgga accttgaact cctgggctca agtgattctt ctgcctcagc   13860
ctccctagca gctgggacca cagagtgcac caccatgcct agctaatttt tattttttcgt  13920 agagacaggg tctcgccaca ttgcccaggc tgatcttgaa ctcctgagct caagcaatcc   13980
tcctgccaca gccttccaag tagctggtac tacaggtgtg taccactatg cccagctaat   14040
attttaattt ttttgtagag atggggtttt ggtgtgttgc ccaggctgag cagtaatatt   14100
ttgaaaggaa tctttttttt tttttctgag cagtaggtct caataatgca cttaaaatat   14160
tcagtatacc gtgctgtaag cagatgtgct gtcatccagg ctttgttgtt ccatttctag   14220
agcacaggcg tagtagattt agcataattc ttaagtgcta aagaatggct taaatgcttt   14280
cagaatggtg aatgagcctt ggcttcaact gaaagtcacc agctacatta gcctctaaca   14340
agagtcagcc tgtccgttga gggtttgagg gcaggcattg acttctctag ctagtaaagt   14400
cctaggtggc atcttcttcc actagaaggc tatttcgtct acattgaaaa cctgttgttt   14460
agtgcaacca ccttcatcac ttatcttagg tagatcgtct gggaaacttg ttgtagtttt   14520
tatattggta cttgatgcct tatcttgccc ttttatgtta tggaaatggg ttcttaaatc   14580
tcatgaacca gtctgctagc tttaagctta acttctgcag cttcctcacc tctattagcc   14640
tttatagaat tgaagaatta ggacctacct ctgaattagg ctttggcttt taagcgaatg   14700
ttgtggctga tttgatctat ccagaccact aaaactttgt ccgtatctgc aataagactg   14760
tttggcttac ttactatttg tgtgttcact gaagtagcat ttctaatttc cttaaagaac   14820 ttttccttg catttatacc ttagcagttt ggtgcaagaa gcctaccttt aggcctgtct    14880
ggagtttcca tatgccctct cctaagttta taaatttcta acttttcatt taagtgaga    14940 gatatgcaac tcttcctttc acttgagcat ttggaggcca ttgtagggtt attaattggc   15000
ctaatttcaa tattgtgtct caggggatag ggaggcccaa ggagagggag agacagaatg   15060
gccagtcagc agcagtaaga atatatacga catttattaa gttcattgtc ttatgggcac   15120
ggttggtagt gccccacagc aattacaata gtaaacatcaa agatcactga tcacatatca   15180
ccataacaga tacaatagta atgaaaaagt ttgaaataat tttagaagta ccaagatgtg   15240
```

-continued

```
acaaagacaa gaagtgagca catgctggtg ggaaaatggt gctgataaac ttgctccaca   15300
cagggttgcc atgaagcttt gattgattaa aaaaatgcaa catatgcaaa gtgcaataaa   15360
gagaagcaca gtaaaatgag gcatgcctgt agttattgtg tgctcttaag gaaattacta   15420
ttactatttt tgagatggag tctcactgtc acccaggctg gagtgcagtg gtgcggtctc   15480
cgctcactgc aacctcgcct cccaggttca agtgattctc ctacctcagc ctcccaagta   15540
gctgggatta caggcgcctg ccaccacgcc tggctaattt ttttgtattt ttagtacaga   15600
tggggtttca ccatgttggc caggctggtt tcgaactccc gacctcaagt gattcatccg   15660
ccttggcatc ccatagtgct aggattacag gcgtgagcca ctgcactcag ccaaaaataa   15720
taagtggtta gtgaatctgt tgttggttca tgtactttta aaaattgtct tccactgggc   15780
gcagtggctt atgcctgtaa tcccagcctt tgggaggcca acgcgggtgg atcacctgag   15840
gtcaggagtt tgagaccagc ctgggcaaga tggtgaaatc ctgtctgtac taaaaaaaaa   15900
aaaaaattag ctgggagtgg tttgcatctg taatcccagc tactcaagag gctgaggcag   15960
gagaatcact tgaacctagg aggcggaggt tgcagcgaac cgagatcgcg ccattgcact   16020
ccagcccgcg caacaagagc gaaactctgt ctcaaaaaaa aaaaaaaaat tgtcttccat   16080
gaaaaacagc atggatgatt tatgagcttt agtttaagcc tgctttgttt gtaatttcat   16140
gttactacag tggttatgat ggcctgtatt caagaatgtt gagtctgtgg gtcatttatc   16200
ttatagctga ttattttata gtgggttgga ataaggttg tgggatttct gaatccaaac   16260
cagaatgctg agaggacatt ggtaataaga tagtgtcctc agtggtgcat gcctgcagtc   16320
ccagctactc gggagactaa ggtgggagga ttacttgagc ttgggagatc aaggctgcag   16380
tgagccgtga tggtgccgca ctgcagcctg dacaacagag caagaccttg tctcaaaaaa   16440 aaaaagatt ttaaaagta tcctcaaaga ttgcttttct tcaagttaat ctgcaaattt   16500
ttggattcta ggacagtatg agatgttaac ttcccacagt tacttgtgat aaggtcttac   16560
taagagaatc gcctcattct agtttraacc ttgttcttgg aagtttatac caaattttg   16620 tttgcttgaa attcattcat ttcagtctat accatttgac tgaatttcag aagggttctg   16680
ataaatcaaa accagtgtgg tactaattac attcttttt ttcttttttg ggatggagtc   16740
tcgctttgtc acctaggctg tagtgcagtg acatgatctt ggcccattgg gttcaagtgg   16800
tgcccctgcc tcagcctcct gagtagctag gattacaagt gtgtgccacc attcctggct   16860
ttttagtaga ctgggttttt cactatgttg gtcaggctgg tctcaagctc ttgacctcaa   16920
atgatccgcc tgccttggcc tcccaaagtg ctgggattac aggcatgagc cactgtgctc   16980
ggccctaatt acattctttt aaaaacttta tcttaatttt tttcccagat gttgaccata   17040
ttagctaaga aatttgaggt cctggaaaaa tgttttaggg gaagcaaaag gtttggtatg   17100
catgttttgc ttttgcttgt ctttcagttc ttaattcagg tgatatgaga ctttacagaa   17160
gtcaaaatgc cagagtaaaa aggtggttat taaaaataaa aaacctcaaa tgtcaaaatt   17220
aagttactta aaagtctggt tctaccattt actttgagta ttaaactaga cagttgagat   17280
tgtataacca tctttgaaaa tgatggttgc taaaggtctg gaggctctgg aggtgatcca   17340
taaagccgct cttattaggt gctttcagga tttataaggc ctaagtcctt gtgatagcac   17400
agcttatctt tattttgttt ttagtttttt tttttgagat ggctgtctac caggctggag   17460
tgcagtggta tgatcacggc tcactgcatc cttgaccgtc ctgggtcaa gtgatcatgg   17520 ctgactgcat ccttgaactt ctgggctcaa gcgattctcc tagctcagcc ttttgggtac   17580
ctaaaactgc aggtgtgtgc caccacagat ggctaatttt tatttttatt ttctatagag   17640
```

```
agggctctca atatgttgtt gcccaggctg gtctctgaac tcctgagcat cctcccgctt   17700
ttaccttcca aagtgttggg attacaggca tgagccgctg cacttgccaa aatgatcttt   17760
ttttttttga cagagtcttg ctctgtcact ctggctgtag tgcagtggag cgatcttggc   17820
tcactgcaac ctccgcctcc caggttcaag ctattctcat gcctcagctt cccaagtagc   17880
tgagattacg ggcctacacc acaacaccca gctgttttgt gttttagta gagacggggt   17940
tttaccatgt tggccaggct ggtctggagc tcctgacctc aagtgatcca ctcgcctcag   18000
cctcgcaaag tattgggatt tgggattaca ggcgtgagcc actgcaccca gcccaaaatg   18060
atctttata tgaacatctg tagcttttat tgttctactg ttctggtgta gtctgtttta   18120
ttgttgtaac tatctgagag ctggtaagtt gagaccaaaa caacaacaac aaaacaacca   18180
aaatcatgct taaaactggt tctttccaag gttgcatttt tgttaagatc tacttaatag   18240
ttgattggat gatttttttt tccccctcc ggtctgaggg atggttgctt ctactgtata   18300
ccactgttat cgccagtatt taattatatt tgttctggtc tgtgaagttt ggtaggaagg   18360
gaagaaagag ctctggttgg cttttctaga ttgacaagtt agaaatttca cttaagagtt   18420
aactgttctt tttattttaa aggacaattt gataatgtca acatttaaaa accaaactac   18480
tagatacact agttaagttc acttcatagt atcttctctc aggaaatgtg cctgcatatg   18540
tatacagagg agaaaatacg aggatatata ttgctgtagt ttcacacccc tctgcccttg   18600
taattggtca ggggaatact ctgcctccac tatgagaaaa taaccagctg tctcaataaa   18660
tgttatgtat tattatatat tgttagaaaa gcaggctgct gaacaatatt gtttctagtt   18720
taaaaatgca aaggaaaact attgtttctg tagacataca gtatgtgtgt aaactttgta   18780
aacaaagttt taaggatat acagacactc cccaatttt cgacttaatg atggtgtgaa   18840
aatgatagct attcaatata cccctcagtt tatgatggga ctacatccag ataaatatat   18900
cataacttga aaacattgta agctgaaaac acactgttga ctcgattata tttacgatag   18960
gattatctgg atgcagctgt gttacaaatt gagcatctgt acatcaaaat tttattggta   19020
actttgccca aaggggggtgg gattgtgtag ggtgctcaaa gggaacattt catttttatct   19080
gtgccgaaat tttttacaag aatgtattac taatttgtat agtttaaaaa atagataaca   19140
ctgtttatcg gtgtgatttg cctaaattga aataaaagca acaaatagca tttagactta   19200
attttccttc atgatttgaa tagaaaattt gagtcagttg tagtaaggaa cttcaggcag   19260
tcctgaaagt caacttttta ttattaatac agagaatagc tttgcagata aacagatatt   19320
cacagaagta tattaacatt taacttctga tagcttaaa tgtgaaaatt acatcatggc   19380
aagatttaca tggtatataa ccatctgttt gcttatgtca tgcccttttta aaacttctga   19440
ataacttttg caagtttctt ctcagtgtag gacttatttc atttagttat tttcattaat   19500
atatgatagg tgttaaaaaa acactagatg tggtattaat gccagacaga cttggtaatg   19560
gaataagcct agtgaatttg tgtttttttag tgatagtaaa tgggaagttg gaattaccct   19620
gcagagaaaa atttcaaat gaagtaggat ttgataataa tgggttgtac atatttctta   19680
ataggtatct caggccagta tagtggctaa cgcctgtaat tcagcacttt gggaggcaga   19740
ggtgggcaaa tcatttaagc tcaggagttt gaggccagcc tggacaacat ggtgaaacct   19800
cacctctaca aaagtgcaa aataggcata gtggtgcaca cctgtggtcg caattgttca   19860
tggagactga ggcaggagga tcgtttgaac ctggaggtg gaggttatag tgagccgaga   19920
tcatgccact gtactccagg ctggtctgga actcctgggg tcaagccatc cacccgcctt   19980
```

-continued

```
agcgtcccaa agtgcagtgg ttcttaaact tggttgcaca ctgggaaaag gaggggtggg    20040
ggtgcttaaa aattattgat ggcttgattc cagtctccaa aattctgact ttattagggg    20100
aaggaatggg cattggtgtt tttgttttg ttttgagaca gagtcttggt ctgtcaccca     20160
ggctggagtg cagtgatgcg atcttggctc acggcaacct ccacctccca agtttaagca    20220
attctcctgc ctcagcctcc caagtagctg gtactacagt catgcaccac catgcctagc    20280
tagttttttt tattttagt ggagatgggg tttcaccatg atggccaggc tggcctcaaa     20340
ctcctgacct caagtgatcg gcccaccttg gcctcccaaa gtgctgggat tacaggtgtg    20400
agccaccgcg cctggctggg cattgggatt tttaatgtgc agctaagatt gcataccaat    20460
gctttgaacc cagtccttgt catctgtggt tgtcatggct cattagcaac aattctctgg    20520
taatttgttt tggtatctta tgtaaagtgg tctctcccag ttttcctctc tctttccttt    20580
gtgacactta acacagtgta cttttggctt ggttacttgt ttgtggtcct tctcccctct    20640
acggtagtgg gaatgagcca tcttgttcac cactatatgt ccagttgcta gcatgggct     20700
ggtacagatg gttgagcaaa tgattttctc acaggtatga gccacagtgc ttggccaaaa    20760
acatgttttt aaaaagtcaa acagggctga ggtgaggtgg cttatgcatg taatcccagc    20820
ccttgggagg atgagggtgg aggatcacgt gagaccccgt ctctacaaaa agtttgtga    20880
aaattagcca gccatggtgg cgtgtgcctg tggtccccac tactgaggtg ggaagattcc    20940
tgagccaaga agatccaggc tacagtgagc tatgatcata ctactgcact ccagcctggg    21000
tgacaaaatg agaccctgtc tcaaaaaaag aaaaaaaag aatcttttgag tgctgcattg    21060
tagttagaac tctgaaggta aggaagtaga tacctgaatg tcctgttcca ttttcattgg    21120
ttttatgtga cagctaacaa ttagtattta attagatggc tatttgatag gttttaaaa    21180
aactcctggt attgatgata ggaatgcata ttttttccct aggtaacagg gtgagatagc    21240
taatggatta taatcatatc tcacttattt taatgggttc ataaatgcct gcaattttat    21300
cttagactga gtctgcccct taagctacat taagtgtaag taaacaaatc tttgttaata    21360
ttgtttaatg ccaaatgtat tgccttattt ttgtctccca tctgtaggct aaagaaatcc    21420
tgacaaaaga atccaacgtg caagaggttc gatgtccagt tactgtctgt ggagatgtgc    21480
atgggcaatt tcatgatctc atggaactgt ttagaattgg tggcaaatca ccagatacaa    21540
attacttgtt tatgggagat tatgttgaca gaggatatta ttcagttgaa acagttacac    21600
tgcttgtagc tcttaaggta atttcaattt tatgttgggg catgttgaaa tgggtaagac    21660
agtcctcttg aaagttttt tcccccagt tattttctct atctgaatgt taaaacaaaa      21720
ttccacattt aggaatgcat atgttcaggt tttggactta aaaatcatag gcgtctgcgt    21780
tctgagtaag gggatggtac agaatcaaaa caaaggagg agaatgaatg cctcagtcag     21840
attgtttgaa aaaataggct gggcgtgatg gcttatgcct gtaatcccag cactttggga    21900
cgctgaggta ggcagatcac ctgaggtcag gagttcgaga ccagcctgga gaacatggtg    21960
aagccccatc tctactaaaa gtacaaaaaa actagccggg ggtggtggcg ggtgcctgta    22020
atcccagcta ctctggagcc tgaggcagga gaattgcttg aacctgggag gtggaggttg    22080
cagtgagctg agattgcgcc actacacgcc agcctggaca acagagcgag actgtctcaa    22140
aaaaaaaaaa ggaaaagaaa aatgttagag ggctggtcaa atagatattt tagttcagta    22200
aattggggta tggagaggta atataattag atttgtgttt ttagatactt ttgaagtatt    22260
ataaatatat aaacatacca aatgtcaaaa tgttttaaat cagctggtca cggtggctcg    22320
tggctataat cccagcactt tgggaggaca ggacaaagtg agcatattgc ttgagtccaa    22380
```

```
gagtttgtga ccagcctggg caacatagtg agaccttgtc tacaaaaaaa taataataat   22440
taaccgagtg tggtggcaca ggcctgtagt cccagctact caggctgagg tgggcagagt   22500
tgcttgagcc caggaggtcg tggctgcaat gagacttgat cttgccaccc tacactctaa   22560
cttggggaac agtgagaccc tgtctcaaaa aaaaaaaaa aatatcgagg aagaagttca   22620
agaaaaaaaa gaattttcct gagaaattca agaaaacatt tgctgtaaat atttaacaga   22680
gaatattatg tacattacat acattatgta tgtacatatg gtttagctca gttgaatagt   22740
ttccagccat taaccatgac agtaataatc tagaataggc tgggtgcagt ggttcacgcc   22800
tgttatctca cactttggg aggctgggga aggcgggaag gatcacttga gtccaggagt   22860
ttaagaacag cgtagtcaac ataaacccca tctctacaaa aagtttaaaa aaatagccag   22920
gtgcagtggt gcatgcttgt agtctcagct actcaggaag ctgaggtggg aagatcactt   22980
gaacctggga ggtcaaggct acagtgagcc atgatgcacc actgcactcc agccgtgtga   23040
cagagcaaga cccctgtgtc tttaaaaaac aaaaatctag aatggtagaa atgataaccg   23100
aaaaaagcaa gttccaaaat tacatgcatt acatgccaat tgtagctttg caaagtgtac   23160
cgatgatgat ctgaacatga agcaaagat ggtaaagagc tgttagggtg gcaggcttcc   23220
gcctttccct tgaaataaat tgtttgactt tacctttacc caaaaatctt ggggagattt   23280 ttttcccct aggcaacaga ctgattttta ttattaaaga atattcaaaa tgataaatgg   23340
ctgtcacaga ctttcctaat attagagaag cagtgagatg tggttttagc gtgagctgaa   23400
ttttcttgat taatatctga attgtgtaaa gtcctacgaa atattttggg agatcgttat   23460
tttctgcatc tgtaaaatga aggagttgga ctagatggtg gaaggtttct gcggtgactc   23520
caaatactat gaaaagagct aacctgtgct aaaaacccag gatgaatccc agtgctcaga   23580
ggaatgaatg tgctacctt aagagtatgc aagcagcctg ggcaacctag tgagaccccca   23640 tctcttcaga aaacaatttt agccagacat ggtgacatgt gctgtagtcc tagccactct   23700
ggaggctgag gtgggaggat tgcttgagcc taggaatttg aggctgcggt gagctactcc   23760
actgcatttg agcctgggcg acagagtgag atcctatctg gggggaaaaa aacttactca   23820
tggaggttaa tgggctgaat tgtagccccc aaaattcatt tgtctaactc ctaacccaca   23880
gcacctcaga atgtgactgt atttggacag gtaattaagg taaagtgggg tcacatggtt   23940
ggaccctaat ccagtgtaag tggtatcctt attagagatt aggacacaga tggggagaag   24000
ataagacaga tggagaagat gagcatccat aaatcaagga gagaggccat cagaagaaac   24060
caactgtgct gacaccttga tcttggactt ctgcctctgg aacagtgagg aagtaaattt   24120
ctgttgttta agccacctat tctctgatgc tttgttgtgg cagccttagc aaaagaatac   24180
cgggggaaag gatgtttctt tcagtaaatg gtgctgaagc aaatggatca gaatgtatca   24240
tagaactaaa tgtaagagct aaagctacaa aacttctaga ataaatcaga aaatctttgt   24300
caggttagtt aaagattctt agatataaca aaagcacagt ccataaaaaa ttgaaaaatc   24360
ggactttatc aaaattaaga ttatgttttt tcaaagatg acaccagaaa aaagtactt   24420 gtattcagat atttaaaaaa aaaaaacttt tacagctcaa taacaagaca gataattgta   24480
aaatgggcaa atatttgaa tagatatttt acccaagaag atgatacatg agtggtcagt   24540
gagcacatga aaagatgctt gatatcaatt gtaatcaggg aaatgcaaat taaagtaact   24600
gagttactac ttcacatcta ttagaatggc agtaatcagt aaggttgata ataccaagtg   24660
ttggttaata ccggagatta aactcttcat gcattgctgg tgggaatata acatggtcta   24720
```

```
gctactttga aaaacagttt gactgtttct caaaaagtta aacgttacca ggtgatccaa   24780
caattatatt cttaggaatc ttcctaaaag aaatgaaagc atatgtccac agaaaaactt   24840
ccatgtgtat gattatagca acattattca tagtagccaa aaacctcagt aacataattg   24900
ccagttcatc ttaactgtga atagagaaac aaaaaatggt atagccatac agtgaaggac   24960
tgtgcaacta tgaaaaggaa caaaccactg atctatgcca gaacatgggt gagcctcaaa   25020
aatattctaa gtgatatttta gccaaaagac tacattttgt attccattta tatgacattt   25080
ctagaaaaga caaactcaag acagaaagta atcagtggt tgccaggagc tggagtggga   25140
gtggagagtg actgcaggag ggatcttttt gggataatgg aaaggttcta aaactggatt   25200
gtggtgattg ttgcataact ataaatttgt gaaaaattac tgaaccgtaa agtaatttat   25260
ggggttttaa tagcccattg atttatgttt ggtataaagt tggtggtaga gggagtttga   25320
ttttagttga gatgaggtgg gcaaacaccc catgggcatt taaaaattct gtagagctgt   25380
ggttttggtt cactatgata tgaggatgtg tgctgttttt tcaacaaaat tgtaactgca   25440 ttttttttcta tagaaagttt cttgaatttt cattggtttt tgaaagagct agttgtttat   25500
gttttgcatt ttattgtttt aggttcgtta ccgtgaacgc atcaccattc ttcgagggaa   25560
tcatgagagc agacagatca cacaagttta tggtttctat gatgaatgtt taagaaaata   25620
tggaaatgca aatgtttgga aatatttttac agatcttttt gactatcttc ctctcactgc   25680
cttggtggat gggcaggtat gtggatctaa aactcattgc tgattatttc agagaatctg   25740 cttttctttag tgttccggtg cttatgactc tttccactct taacaccct tgggggttat   25800 tttttaatag atattgatag cattcattca aacttaaaaa aaatttaatt tgacaaatgt   25860
gtccaacttt tttaagtgca ttattcttta tatcaggcac tgaactgtat ggtgggatca   25920
caggggtggg tgatgtagcc catttacccct ctcagactgt ttttggacaa gtctgggaga   25980
tgtaaggagc taattattgg cctaggtaga tgtgcacaca aaagaactta caataaaatt   26040
ttatgagtat gaagatacta gtctctggca agggcagga gtgatatcca agaagttttc   26100
tcaaaggagc tgtttgaagt ggagtctggt tgtgacagcg atggtctatt aggaagaaca   26160
ggagtgtact caatagttca gagtgggctg gagcaaagat gaaccctgca aagtcaagtc   26220
tcattaaggc agagcacaga aacaccagag gggccaagtg atgggggtgc ccagctcatt   26280 tttttaaaatt tttgtagaga cacagggtct tgctgtgttg ctcaggttgg tctcaaactc   26340
ctggcctcaa gcagccctcc tgcctcagct tcccaaagtg ctgggggttac aggcatgagc   26400 cactgtgccc agccaagaat gtttacaaat ttttttaggtg aggttaaccct tttaaaccac   26460 tcttttcaga tcttctgtct acatggtggt ctctcgccat ctatagatac actgaatcat   26520
atcagagcac ttgatcgcct acaagaagtt ccccatgagg tatgacttt tatttgataaa   26580 attcttttcag aaaacttatt agggagtgga gaagtttaat tgtaagttca ttagatgtat   26640
tctctcatat aattctcaaa acaacttga ggtgtgagca ctcttgtctg ccctgttgtt   26700
caaaagaagc tgacattaag aaacctgcca agatcacaac agctgtgaag ctgggcttat   26760
taggacctgg gttgtctgtc ttagactctg aaatttgcat aatataggca gattaattag   26820
ggcatgttgc tgctgggtcc catggatgtc agctgtgtct cataaagtct gctgaaaat   26880 acatcttatt tgatgcagat gtttgacttc aactgcacag tctattagca ttgtccacaa   26940
acatcactca aaagggtgg cttaggggtgc tgcttctgat gaattactca aataatgtgt   27000
taaccatgtt tgtaaaaggc attttataac ttgaagttat ttttagggt ccaatgtgtg   27060 acttgctgtg gtcagatcca gatgaccgtg gtggttgggg tatatctcct cgaggagctg   27120
```

```
gttacacctt tgggcaagat atttctgaga catttaatca tgccaatggc ctcacgttgg   27180
tgtctagagc tcaccagcta gtgatggagg tatgctgtgt tctctgaaat atgacttgtt   27240
tttttagtaa acttaaggaa agaagatatt agggagtttt aaattaatga catttgtgag   27300
aaattccatc tattccttct gatgagttta tcattatagc ctgagccttt tcagtagatg   27360
cacactacta gaattaaaag ctcaagcttt tgattacaat gaatccatta acatgttttc   27420
agagaaatct gaatgactag gaagtacttg agatttaaga gtgggaaagt aagatatagg   27480
gagttggtgt gcatgtatga tattttatga tcccaatgtt atttcgtata tttaatgtat   27540
gtatgtagga gagactggaa agaaatacac gaaaatgttt taagtggtcc tttggatgct   27600
aggattacag gtgatttgaa agaagggaaa gaggcaaagg ttcttgacat ggcacactga   27660
ttagaatatt tttaaaataa ggtcctaatt agattaatac tagtacaact ctgtggttat   27720
caataaaatc tgactttgct aaaggtaaag aaatttgtga acaatactaa acaaaaagta   27780
acaaaagtag ctcatgcatt caggtggatg gactttgagg aaatgaggct ggagatccta   27840
gaggcatatt gcatttgttc ctgggcagtg accaacttaa caggcccttta cctgtgactg   27900 acaaaattgg taaggttctg gtctccagga ttaagtatct acttctctag ggaatggcca   27960
cttaaatact tattccttaaa tcatgtttta aggccactgc aagagaagag gctaatgaga   28020
cattgtcatt tacagcaagg cagatacatg agaagtattt cattctttgg tggttgctgc   28080
tgtttgttaa agcctttttt ttttttaaag tactaaaaaa aaaacaagtt ttgtaattag   28140
ggggaaaata aatacatgtg taccttacag gttgtataaa gtacaggaga ttattaagtc   28200
atccagaaaa aaagcattaa catttcttaa gccccttttgg caggggtggg aatgagtaga   28260 gattttttttc tctcttgagt gaagtaacat ttagttgaat tgagggagta aagtaagatt   28320
tttgtctcct tttccttgca gggatataac tggtgccatg accggaatgt agtaacgatt   28380
ttcagtgctc caaactattg ttatcgttgt ggtaaccaag ctgcaatcat ggaacttgac   28440
gatactctaa aatactcttt gtaagtaatt ctacctgaac atttttcttgc attactgaat   28500 atgtagggtt ttggtttatt tattttgaga gagagggtgt cactatattg cccagtcttg   28560
tctcgaactc ctaggctgaa gtgatccttt caccttggcc tcctagagtg ttggggttac   28620
aagtataaga tacagtgccc agcctgaata catagtttaa atgtgaggtt taagagttta   28680
agggggccag gcgcggtggc tcacgcctgt aatcccagta cttttggaagg ctcgggtgga   28740 tcacctgaga tcaggagttc gagacaagcc tgaccaacat ggtgaaaccc cttctctact   28800
aaaaatacaa aaattagccc agcgtggtgg cgcctgcctg taatcccagc tactcaggag   28860
gctgaggcag gagaatggca tgaatccggg aggcagaggt tgcagtgagc caagatcgcg   28920
ccactgcgtt ccagcctggg caacagagcg agacttcgtc tcaaaaaagt gtttattaag   28980
ggattatgct atgtcagatt ccaacttttta tttttaagtt ttgtttttttt tttaatggat   29040 ctacattgaa acacaccaac aggaacttat tatatataga tcttcgtatg aattactagg   29100
tttttcactt ttaaaaccat gttttgtgtt tttttgttgt ttgtttgttt gttttttgag   29160
acggagtctc actctgtcac ccaggctgga gtgcagtggt gcgatcttgg ctgactgcaa   29220
gctctgcctc ccgggttcac accattctcc tgcctcagcc tcccgagtag ctgggattac   29280
aggcgtctgc caccacgccc ggctaatttt tttgtatttt tttagtagat atgggtttc   29340 accgtggtag ccaggatggt cttgatctcc tgacctcgtg atccgcccgc ctcagcctcc   29400
caaagtgctg ggattacagg cgtgagccac tgcgcccggc caaccatgtt ttgttttgtt   29460
```

```
ttgtttgaaa tttcagtcaa ggtaaaaacc atgtttttat aaaagcatag tctctgtggc  29520
tgaagttgcc ttgactcttt caaggggagt acagttaaca gaccattatc attaaggttc  29580
tgttacatta agacaagcca aaattgaata ggaagtgtaa agtttggaag actcatgttc  29640
ttgatcttga ttgtcactac atggaggtcg tggaacataa accatgaatc ggtcttgttt  29700
ttcagcttgc agtttgaccc agcacctcgt agaggcgagc cacatgttac tcgtcgtacc  29760
ccagactact tcctgtaatg aaattttaaa cttgtacagt attgccatga accatatatc  29820
gacctaatgg aaatgggaag agcaacagta actccaaagt gtcagaaaat agttaacatt  29880
caaaaaactt gttttcacat ggaccaaaag atgtgccata taaaaataca aagcctcttg  29940
tcatcaacag ccgtgaccac tttagaatga accagttcat tgcatgctga agcgacattg  30000
ttggtcaaga aaccagtttc tggcatagcg ctatttgtag ttacttttgc tttctctgag  30060
agactgcaga taataagatg taaacattaa caccctcgtga atacaattta acttccattt  30120
agctatagct ttactcagca tgactgtaga taaggatagc agcaaacaat cattggagct  30180
taatgaacat ttttaaaaat aattaccaag gcctcccttc tacttgtgag ttttgaaatt  30240
gttcttttta ttttcaggga taccgtttaa tttaattata tgatttgtct gcactcagtt  30300
tattccctac tcaaatctca gccccatgtt gttctttgtt attgtcagaa cctggtgagt  30360
tgttttgaac agaactgttt ttttccccttc ctgtaagacg atgtgactgc acaagagcac  30420
tgcagtgttt ttcataataa acttgtgaac taagaactga gaaggtcaaa ttttaattgt  30480
atcaatgggc aagactggtg ctgttttatta aaaagttaa atcaattgag taaatttag  30540 aatttgtaga cttgtaggta aaataaaaat caagggcact acataacctc tctggtaact  30600
ccttgacatt cttcagatta acttcaggat ttatttgtat ttcacatatt acaatttgtc  30660
acattgttgg tgtgcacttt gtgggttctt cctgcatatt aacttgtttg taagaaagga  30720
aatctgtgct gcttcagtaa gacttaattg taaaaccata taacttgaga tttaagtctt  30780
tgggttttgt tttaataaaa cagcatgttt tcaggtagag cttaaactaa atgatgtgtt  30840
tacttagtgc agtttctggt tatgaatatt atattgctat gtgtatatta tatggactct  30900
ttaaaatgat tgacagattg gcaaattctt aaatctttgt acattgttga gtcatatgtt  30960
cttagagtta aatttgtctc agataagaaa gtgttaaagc attagcctgt gtcaagttct  31020
ttgagtgata ctagtgaaac caaatagaaa actattgttg gatcatgatt tagtcttatg  31080
tacattcacc cgaagacaaa aatggtactt aaagtggcag tgttcaacat ttaatgagtt  31140
tttccccttt tatccttcga ataggattag atgtttaaaa aaaagttctt ctgtgggaac  31200
taatatttga tattttaacc taccagagta aacaggaaca cttaatcata cttgtgagtg  31260
tagtaaataa aagttttctt gctttgtgct gtgttgaatc tggaaccaac agggaagtta  31320
tagcatatcc cctttctaaa atgcttgagg aacacataca taccgaatgt ctttttctgat  31380 ctaattgata gtattttag tggcttgtgg agttaatttt ccaaagcaaa aggccattag  31440
ggtttctaca tttcatttca tttcattctt tcctttcaca agaaatacat tctctgtgtg  31500
tctttttgtt gctctgtcac tctatgccct ttctctccga ctgaacaaat agcttatcca  31560
tgtgcagtgg ttttaatacc caaacaatct agacaccaag cagctatttt ttccggtcct  31620
gtgatatcag aattgaccaa ggaatacgta tattgtaatt gacacgtggt ggtatcttcc  31680
aggtacaaat tctctaaatt ttgtggttag cagaatggga cttgtgataa gaatagcttg  31740
gttttagcat aactagggtt taaaataatt gtttaattat agagactgac caggctttgg  31800
ccatctaaac tggaaagtgt tagtacccta ccttcttttg aaaatggcta tggtaaggaa  31860
```

```
aatgtgttag taaattatgt attttcttga aaaatacata attatggttg gatgggaatc    31920
actaagttgg gtgttaactg atgtctcaat tagtaacatt aggattttca ttaataaacc    31980
taaaaagctt tccctaagaa caggcctggc acagtggctc atgcctgtaa tcccaacact    32040
ttgggagacc agggtgggtg gatcccttga ggtcaggagt tgaagagcag cctggccaac    32100
atggcaaaac cccatctcta caaaaaatat gaaaatcagc cgggcttggt ggcataccat    32160
agtcccagct acttgggagg ctgaggtgag aggatcgcct gagcccagga gacggaggtt    32220
gcagtgggct gagattgtgc cactgtactc cagtctgggt gacagagcca gaccctgtct    32280
caaaaataaa gaggattctg agtttgtata gtgagggctt gcagaaattt tgaaacttat    32340
tttgtaagtt tacaatgaat ttgtacatga tgtgctcatg tcttggggttg agtatcctag    32400 acatgatttt ttcatttgct gcatattaaa catttgttgg ttgtagtcgg tatttcttaa    32460
atagaagttt gtcaatatta gattagtttc aagaaggact tagctcagga aaaggatagt    32520
tatttctgtg gttctcagct ttgatgccta cagagattct gatttaaatt gctggaggag    32580
ggcccaggca tacatttttt aagtttccca agtgattcta atttacatct agggttaaaa    32640
acagccaggc gcggtggctc atgcctgtaa tcccagcact ggggaggcc ggggtgggtg    32700 gatcacctga ggtcaggaga tcgagaccag cctggccagc gtggtgaaac ccatctcta    32760 ttaaaaatac aaaactgacc ggtgtggtgg caggagcctg taatcccagc tacttgggag    32820
gctgaggcag gagaatcact tgaactcagg aggaggaggt tacagtgagc cgagatcgtg    32880
ccattgcact ccagcctggg caaaaagagc aaaactccat ctcaaaaaac aaaaacacct    32940
cactgctgtt tcctaagtac atacttaaga aaattgggat acatggtggt ggttcatgga    33000
tgttgataag gaattaaaat gtaccgtgcg actctctgtt tcagtggtga cttttacctg    33060
tttagtataa atattccttt gcttccaacc ataaatgtgt tcttagaaat gggcctatag    33120
tttagtaacc tatagtttgg taataggctt gtttgttttc agatggattt tggttctgtg    33180
agctaaagct attttgcatt aaagccttcg tcctcacaca ttgttttgac atatttctag    33240
tcttcataaa cttttttaat ttagattttt ttcccttcac aagtatacat ctgttttagc    33300 aaaatagcctt atgaaggttg tagatgtatt attttgggca tgcctggtga tttctatatt    33360
ttttccaatt acatttaaag ctttatgttt taggaatata agtacatttt atttctactt    33420
tttattatat atatttaatt gcacaagtac tactgtctag aaaaaaatgg gatgttgcta    33480
acacagcatt gttggcttgt aggcagtgct gtcctgtaaa tagattgaaa tgtatttta    33540 tcagctggta tataaatttg aggaaagaaa aatgtggact gtgtttgaat tgtttaaaag    33600
ttgaacatac aaagatcagt ggtaaccaag taagtgatat aggcaacaga ccccagtttg    33660
ttttgtattt gctgtcatgc ctggaccaga attcctcatt cccaagacgt gaaagaggaa    33720
ataattatag ctaaatgagt gaatgctgga aaaagtcaca ctttttttgtt ttttaaggaa    33780 aagcacaaac cctcatgtct gaggttgaat ttaattaagt gcagtcggcc ctccatagtc    33840
aagggttcca catctgagaa ttcagccaac catggactga aaatatttt gggaaaagga    33900 accaataaaa accaatacag tggccaggag cagtggctca tgcccataat cccggcactt    33960
taggaggcgg aggcagggt gggggatca ccggaggtca ggagttcaag accagcctgg    34020
ccaacatggt gaaacccccgt ctctactaaa aatataagaa ttagctgggc atggtggcgt    34080
gtgcctgtaa tccagctac tcaggaggct gaggcaggag aatcacttga atctgggagg    34140
tggaggttgc agtgagccaa gatagagcca ctgcacttca gcctgggcaa cagagcaaga    34200
```

```
ctccgtctaa aaaaaaaaaa aacacagtat aactatttac atagcaattt cattgtttag   34260
gtattatgag taatccatat tttaaagtat agccagccat caagtatcca cagagtttgc   34320
atcaaatgag tcaatggagt caaccaacct gggattgaaa atgcagtgtt cttttttttt   34380 tcccctgag acggagtctc tctctgtcac ccgggttggg gtgcagtggc acgatcttgg    34440
ctcactgcaa cctgtgcctc ccgagttcaa gcaagtctcc tgcctcagct tcccaagtag   34500
ctgggattac aggcgcggct cactacgccc agttaatttt gtattttttag tagagacagt  34560 ttcaccatgt tggccagggt ggtatgaaac tcccaacctc aggcgatcca cctgcctcag   34620
cctcccaaag tgctgggatt acaggcatga gccaccgcgc ctggccaaaa aatgcagtat   34680
tcttgaatgc agaacccact ggtaaagggg actgacttcc agacttgact atccaaggga   34740
ggtgtcctgg atccagtctc ccaagattac tgagggatga ctagtttgta tcctcaacag   34800
gcttgtgaga agtagccagg attttgtcta ctctgcgtac gatgctgcta atgctgcaaa   34860
ccactgctct tattttacta cttgggtccc ttcggaatct attttgagat agcctcagcc   34920
atgatgtaca atcttctcaa ccattcagtg ttgttagtgg gaaggacttt aatgtgttct   34980
tcctgctggg cacagtggct cccgcctgta atcctatcac tttgggagtc cgaggtgggt   35040
ggatcacttg agcctggagt tgaagatgag cctggccaac atggtgaaat cctgtctcca   35100 ctaaaaaac aactagctgg gtgtgatggc acttacctct agtaccagct agttgggagg   35160
gtgagactaa atcgcttgaa accgggaagc agaggttgca gtgagctgag atcgcgccat   35220
tgcactccag actgcgagac tcttgtctcg aaaaaatata tttttaaaag ctttcttcca   35280
agaaataatt tagctgttct tccttagtgc agtggtaggc tgtagccacc agcaagcaag   35340
attactgatg gtggaagtca aaggccagaa tcgtgatagg aagttaagag tgcttgctcc   35400
atagaacact atggaagacc acaatggaat gtctaattaa agctattaga aatgcccaaa   35460
gctgttgagt gcctctacct caaggcttag cataccttct gatctgcaag gagactaatc   35520
attaggcttt ttgcagttct agaactgctc tgagtatggc attggaacct ggggatagga   35580
gcaagagcta gtaattgggt ttggcaggcc tggtcaaagg ggagctttaa ggtcaggtat   35640
atccaaacat atcaggaagt aggttacatg gtgtggtgaa atataccaga tgtaaaatct   35700
gcagaatgta ctcctgctgt tgagtccaac ttgcaatgta agtccctttg cagtgaaggt   35760
cttgagtatg tattgcatgc agcaggcaga ggagcgggag gagaaactgt ataatgtatt   35820
tggtcttgaa catcctttgt tttccaaaac cacattcatc tctaccttgg ttgaaatgta   35880
taaaactacc attttaagtt tcatcttttc attgatctat gactaaaatt aggatgcaaa   35940
gacaaaccca aggcttagcc cactgctcct cctcagagct gcactggaac tggttgtagg   36000
gtaaagggat gtaggcaatt taaatatgag tcaagatttt tgggatggca gtatggctct   36060
catggcctct ggaaggatcc aggtgatgtc cgacctggta tggcctcttg gcctgttgcc   36120
accgcaccag gttttgccct taattttagt cttggctctg gatttcttta gggtattgtg   36180
atagctttgt tggtctttgg gttttttctag tttcaccaca gatcctagga aaaataacca   36240
tactctagaa atgagaagcc aggattttta aagtagggct gggaatatga gtagacatct   36300
tttggatttt caaaatgtat ttgcttaaac cacctttttgg cagcagttgg acatttctgc   36360
tatctacctg agtggcagat ggcctacagc atttggtatg ttaaagagt atagagtaag    36420 tgattcatgg cttctgaaat acatcaattt gacgttgcag tcttgaaaag gcaatagctg   36480
acatatcctg aaccagcttg ggtttccagt gcactcagtg ctgaaataat tgctgtgaag   36540
ggttgagttg aattcagaat gacttaggac agtagtagct actgaatgtt caatctttga   36600
```

-continued

```
aatgacagaa ttagcttata gtgaatattg tctagcactg agcatttcca tgtgccaagc    36660
atgttacatg aattattgag ttttctcaac tctgttgaga agagcagaga aggttctgct    36720
attcaggcat tctgatcgca gagttcctga ttttcaggaa gcattaggtt tctcttgcct    36780
ttgctgaaat tcttattagt ggtgtttgaa gggtgggcaa tagcctacac agctttaggg    36840
tttagatgtg tcgcttagcc ccattcagga agctaggtgt gtgatgggcc ctttggggag    36900
tgtgtggtga ggaaggcttg catgctgggc cttttgagtg ttggcccaag tcaggtagcc    36960
tggttacagc attctcaaga gttcatggac tgccgggcac agtggctcac gcctgtaatc    37020
ccagcacttt gggaggctga ggcgggtgga tcacaaggtc aggagttcaa gaccagcctg    37080
gccaagatgg tgaaacccca catctactaa aaattaaaaa aaaaaaaaa ttagccaggt     37140 gtggtggcgg gcacctgtaa tcccagccac tcgggaggct gaggcagaga attgcttgaa    37200
cccgggaggt ggaggttgca gtgagctgag atcgcaccac tgcactccag cctgggtgac    37260
acagtgagac tcgtctcaaa aaaaaaaaa aaaaaaaaa gagttcatgg actaaccttt      37320
gtgtctcaag gcatttatt tgagccagag tttgaagggg agttaggtga ggttcagctg      37380
aaccaccaca gcctaacaat tgctcttgaa gataaagaa ttttcacagt ggacccgcat     37440
taacaaatac taaaggaaaa ccagaaagta tatgtggagt ggagcacccc atccctaact    37500
tttaaaaatt catctaagtg gcataattcc tccatttttt atctgaattc ccaactgaat    37560
tgtgggtttt cttgaatgac ctgagttttt tagactcttt tataaacttc tgggattctg    37620
tacaagacta ctggaaacta gtcagctctt taggctgaca gttgtagtaa tgaatgaaat    37680
ctcatgctag cctgtcatca cctgaccatc ttcccctcct tctgaagacc cttaccttct    37740
aatctgagag gagccagaag ccaagaccaa cttactttct tgtctggtgt cctgatggcc    37800
agttaacaaa ttctgatacg gaggacttga ccctatgaac aatgcccatc tctaatctgt    37860
atgagtgcac attcttttta aaaatggat cttttctact cgtattaata taaaatacat     37920
gcttgtagta aagcaataga gatgaataca aaaaagttt cccctccagc cttattggtc     37980
tgaggtggtt actactaatg gttgtggatg ttttcacagt catatcagca agtctgctgt    38040 gtgtaggtg gttgtgctct agtcttcctt tcatgatgat gtgtattaaa ttgtttctct     38100
gggagcaata ctcctcgccc ttttaaaaca aatggtaaca gacaccattc cgcacatagc    38160
atattttcat ttagcatctt tggtattaac cagtgtgagc ttttattttt aaagtaacag    38220
tagtgagttg gtggaagtat gatgggttcc tgaagtagtt aaacatggag gcaaaactaa    38280
gtaaactcac cagcttgtta atgtgtggcc acggttgggc acagctccaa tatagggtga    38340
ccagttgacc tggttgctta gaacttgaag gttttccagg aagcagatct tgctttcttc    38400
ttcttcttct tcttcttctt tttttttttt tttgagatgg agtttcattc ttgttgccca    38460
agctggagtg caatgacaca atctcggctc actgcaacct ctacctccta ggttcaagtg    38520
attctcctgc ctcagcctcc caagtagctg ggattacaag tgtacgccac cacacctggc    38580
taattttttg tattttagga agaaatgggg tttcaccata ttagccaggc tggtctcaaa    38640
ctcctgacct caggtgatcc acccgcctat gcctcccaaa gtgctgggat tacaggcgtg    38700
agccactgcc ccagccagta gagctttgaa accagaacag ttggtcaccc caatgtggg    38760 ttctgtgcct ttcccacccc tatcaaccag acaaatccca ggctctgctt tggctctcag    38820
ctgggatctt gggggtgggg aagtggtaac tgggcgaatt tactcagacc tgagctctaa    38880
gactacctgc tgcctggctt gcagtcatgc atccacagga accagtcttt gcattaagtc    38940
```

```
tataactgag acccccagct cccaaggttc caaggtttgt gctacatgct ctcgtttgtg    39000
aggactccaa ggcttcttaa gtctcaaggc aaaggacagg aaggcaaaga tctaagaagg    39060
agaacagagg gttaaattta ttagaatagg aagaaagggg tgaagcaagg tgggtgtgtg    39120
ttgaggggtg agaggttcta gcaagagggc ttaggtctta gccagggtgt atgtagtaag    39180
gggctgctgc catctgggag agcacagcaa gtgaagtggg caagaagaga tgttgccatg    39240
gtatttgagt aacttccact gggtaagtaa gccaccacca ggcaccagct gagctgagtg    39300
gtattcagca gctacttact gtgcacctgt tatgtgccag gcattaggca caagcggtgt    39360
acaagacaaa gtgcccttgt gcagtgaaca cccaagagag acaaatataa aactccaata    39420
ggaataatgt actatgaaga aaagcaaga caggaggcca gagggtaaaa ggaggtaccc    39480
ttctagccaa aacttccaca tactgttgtg cacattgctt actgcccaac tcaagtttgt    39540
gaattttgac aatttttttg gctgatggca atcgtatgtc ttgatgtgat ggctgttaaa    39600
tttttaaaat aagttttaat gtaaatttaa cgtactattt aggctggtgg tctctgagga    39660
ggtgacactg agctgagacc taaggatga gaaggagcta ttccttctca ccaatctgca    39720
ttagatgctg tttatcacaa ggtgaaaaat cacttgtttt gaaagagaat gcggaagtgt    39780
agtttgtaga aaagcactga ccatgacctg ataacattcc tagaaatttc cgccatctgg    39840
ggcagcggtg gggaagctgc tgtttgagag actgctgtag tccaggctgt gctgttctga    39900
ccagagcctg ctgcctacag ctgagtggca ggatgtggct agaggaatgg acacagctgt    39960
actggtggga ctcacacaaa tgtcagatgg accagttact                          40000
```

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
accaaggcag tgagaggaag                                                 20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
caccagtctt gcccattgat                                                 20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
ctcgctgagg ctccagagct                                                 20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 22
ctctcaccgc agtactcggc                                          20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ctcgtgtact tctggcggct                                          20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
acacgcacac gccgccgccg                                          20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
tcccgcgccg ccgcccgcac                                          20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
ctcttgacct gggactcgga                                          20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ggatttcttt agccttctcg                                          20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
tcttttgtca ggatttcttt                                          20

<210> SEQ ID NO 29
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
agcagtgtaa ctgtttcaac                                               20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
aagagctaca agcagtgtaa                                               20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
aacgaacctt aagagctaca                                               20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
tgtgtgatct gtctgctctc                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ttccaaacat ttgcatttcc                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
ctgcccatcc accaaggcag                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
```
gacagaagat ctgcccatcc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
agtcacacat tggaccctca                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
gaccacagca agtcacacat                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
attaaatgtc tcagaaatat                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
cgtgaggcca ttggcatgat                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
cagttatatc cctccatcac                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tagtttggag cactgaaaat                                              20

<210> SEQ ID NO 42
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 42
tgcagcttgg ttaccacaac                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gttccatgat tgcagcttgg                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
tcgcctctac gaggtgctgg                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
cattacagga agtagtctgg                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
tcatggcaat actgtacaag                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
atatggttca tggcaatact                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ctgacacttt ggagttactg                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
ctattttctg acactttgga                                       20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
atggcacatc ttttggtcca                                       20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
tatggcacat cttttggtcc                                       20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gacaagaggc tttgtatttt                                       20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
ggctgttgat gacaagaggc                                       20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aagtggtcac ggctgttgat                                       20

<210> SEQ ID NO 55
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 55
ttctaaagtg gtcacggctg                                          20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gttcattcta aagtggtcac                                          20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
caatgaactg gttcattcta                                          20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ttcttgacca acaatgtcgc                                          20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
cagaaactgg tttcttgacc                                          20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
agcgctatgc cagaaactgg                                          20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
aactacaaat agcgctatgc                                          20

```
<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
aagcaaaagt aactacaaat                                           20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
cttattatct gcagtctctc                                           20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
taatgtttac atcttattat                                           20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
tctacagtca tgctgagtaa                                           20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
agctccaatg attgtttgct                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ttcattaagc tccaatgatt                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 68
atgttcatta agctccaatg                                                    20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
tcaaaacaac tcaccaggtt                                                    20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
acagttctgt tcaaaacaac                                                    20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
ccattgatac aattaaaatt                                                    20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
aattgtaata tgtgaaatac                                                    20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gcacaccaac aatgtgacaa                                                    20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
aacccacaaa gtgcacacca                                                    20

<210> SEQ ID NO 75
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 75
gaagaaccca caaagtgcac                                                  20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
agacttaaat ctcaagttat                                                  20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
aagtgacgtg ctgcaaagtt                                                  20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
agtctttggg ttgcatctgt                                                  20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
atgaatagga agctttcaag                                                  20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
acccagtctc ttagttttcc                                                  20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
```
tccaggcgtg agccactgtg                                            20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
gctgtcgctt aggctggagt                                            20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
gggcgaagtg gctcacgcct                                            20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
agctgagagc agcaagtggc                                            20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
agcttctttt tatatcagca                                            20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
acacaccaaa accccatctc                                            20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ataaaggcta atagaggtga                                            20

<210> SEQ ID NO 88
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 88
acattcgctt aaaagccaaa                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ttgacattat caaattgtcc                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
gtgcagtagt atgatcatag                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
aatatgctca ctttgtcctg                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
cagtggtttg ttccttttca                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
tggcccctct ggtgtttctg                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
acatgttaat ggattcattg                                              20
```

```
<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
cgaactcctg atctcaggtg                                               20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
aaataaaagt tggaatctga                                               20
```

ANTISENSE MODULATION OF PROTEIN PHOSPHATASE 2 CATALYTIC SUBUNIT ALPHA EXPRESSION

FIELD OF THE INVENTION

The present invention provides compositions and methods for modulating the expression of Protein Phosphatase 2 catalytic subunit alpha. In particular, this invention relates to compounds, particularly oligonucleotides, specifically hybridizable with nucleic acids encoding Protein Phosphatase 2 catalytic subunit alpha. Such compounds have been shown to modulate the expression of Protein Phosphatase 2 catalytic subunit alpha.

BACKGROUND OF THE INVENTION

The process of phosphorylation, defined as the attachment of a phosphate moiety to a biological molecule through the action of enzymes called kinases, represents one course by which intracellular signals are propagated resulting finally in a cellular response. Within the cell, proteins can be phosphorylated on serine, threonine or tyrosine residues and the extent of phosphorylation is regulated by the opposing action of phosphatases, which remove the phosphate moieties. While the majority of protein phosphorylation within the cell is on serine and threonine residues (Wera and Hemings, *Biochemistry Journal*, 1995, 311, 17–29), tyrosine phosphorylation is modulated to the greatest extent during oncogenic transformation and growth factor stimulation (Zhang, *Crit. Rev. Biochem. Mol. Biol.*, 1998, 33, 1–52).

Because phosphorylation is such a ubiquitous process within cells and because cellular phenotypes are largely influenced by the activity of these pathways, it is currently believed that a number of disease states and/or disorders are a result of either aberrant activation of, or functional mutations in, kinases and phosphatases. Consequently, considerable attention has been devoted recently to the characterization of these enzymes.

The enzyme protein phosphatase 2A (also known as PPP2A and PP2A) is one of four major protein phosphatases identified in the cytosol of eukaryotic cells which are responsible for the dephosphorylation of serine and threonine residues in proteins. These four enzymes have overlapping substrate specificities and are distinguished by their regulation and dependence on metal ions. Protein phosphatase 2A activity is independent of metal ions and appears to play a role in the regulation of major metabolic pathways, as well as the processes of translation, transcription, platelet activation and control of the cell cycle (Goldberg, *Biochem. Pharmacol.*, 1999, 57, 321–328; Millward et al., *Trends Biochem. Sci.*, 1999, 24, 186–191; Toyoda et al., *Thromb. Haemost.*, 1996, 76, 1053–1062). More specifically, Protein Phosphatase 2A participates as a negative regulator in many kinase signal transduction pathways, including those involving MAP kinase, JNK kinase, ERK kinase, CaM kinase, and casein kinase. In addition, Protein Phosphatase 2A also interacts with many cellular and viral proteins (Millward et al., *Trends Biochem. Sci.*, 1999, 24, 186–191). The enzyme has been shown to be activated by ceramide, a metabolic product of sphingomyelin hydrolysis and mediator of the biological effects of hormones, cytokines and growth factors (Dobrowsky et al., *J. Biol. Chem.*, 1993, 268, 15523–15530).

The mammalian protein phosphatase 2A enzyme is a heterotrimer composed of a catalytic subunit of 36 kD complexed to two regulatory subunits, one of mass 65 kD and one of variable mass. In addition, two isoforms of the catalytic subunit of protein phosphatase 2A, alpha and beta, are demonstrable in many species. The structures of these catalytic subunits show high evolutionary conservation supporting the idea that they may serve crucial functions (Goldberg, *Biochem. Pharmacol.*, 1999, 57, 321–328; Millward et al., *Trends Biochem. Sci.*, 1999, 24, 186–191).

Protein Phosphatase 2 catalytic subunit alpha (also known as PPP2CA) was originally isolated from lung and lung fibroblast libraries (Stone et al., *Nucleic Acids Res.*, 1988, 16, 11365), while the gene was isolated from a human leukocyte library (Khew-Goodall et al., *Biochemistry*, 1991, 30, 89–97). Northern analysis has revealed that the alpha subunit is expressed at relatively high levels compared to the beta subunit in all tissues examined. The structural characterization of the two genes implies that this is due in part to the different strengths of the promoters (Khew-Goodall et al., *Biochemistry*, 1991, 30, 89–97).

The catalytic subunit of Protein Phosphatase 2A has been linked to both insulin signaling (Klarlund et al., *J. Biol. Chem.*, 1991, 266, 4052–4055; Kowluru et al., *Endocrinology*, 1996, 137, 2315–2323) and to retinoic acid-induced cellular differentiation of HL-60 cells, an acute promyelocytic leukemia cell line (Nishikawa et al., *Cancer Res.*, 1994, 54, 4879–4884; Tawara et al., *FEBS Lett.*, 1993, 321, 224–228). The pharmacological modulation of the catalytic subunit of Protein Phosphatase 2A activity and/or expression may therefore be an appropriate point of therapeutic intervention in pathological conditions such as diabetes and cancer.

Currently, there are no known therapeutic agents which effectively inhibit the synthesis of the alpha isoform of Protein Phosphatase 2A catalytic subunit, and to date, investigative strategies aimed at modulating activity of Protein Phosphatase 2A function have involved the use of antibodies, molecules that block upstream entities, chemical inhibitors and gene knock-outs in mice.

Disclosed in U.S. Pat. Nos. 5,925,660 and 5,700,821 are compounds useful as phosphatase inhibitors and methods of making such inhibitors (Lazo et al., 1999; Lazo et al., 1997). It has also been reported that the compound, Fostriecin and compounds structurally related to it are effective serine/threonine phosphatase inhibitors. These are disclosed in the PCT publication WO 98/14606 (Honkanen and Downey, 1998). Disclosed in the PCT publication WO 99/27134 are antisense oligonucleotides targeting serine/threonine phosphatases, PP5, PP4 and PP1γ1 none of which target or hybridize to the Protein Phosphatase 2A isoforms (Honkanen and Dean, 1999).

In addition, at the protein level, there are compounds that interact with and consequently modulate the activity of the Protein Phosphatase 2A enzyme. These compounds and methods to identify these compounds are disclosed in the PCT publication WO 97/37037 (Hemmings, 1997).

Finally, homozygous null mutant mice are embryonically lethal, demonstrating that the alpha subunit gene is an essential gene (Gotz et al., *Proc. Natl. Acad. Sci. U. S. A.*, 1998, 95, 12370–12375).

These strategies are untested as therapeutic protocols and consequently there remains a long felt need for additional agents capable of effectively inhibiting Protein Phosphatase 2A catalytic subunit alpha function.

Antisense technology is emerging as an effective means for reducing the expression of specific gene products and may therefore prove to be uniquely useful in a number of therapeutic, diagnostic, and research applications for the modulation of Protein Phosphatase 2A catalytic subunit alpha expression.

The present invention provides compositions and methods for modulating Protein Phosphatase 2A catalytic subunit alpha expression.

SUMMARY OF THE INVENTION

The present invention is directed to compounds, particularly antisense oligonucleotides, which are targeted to a nucleic acid encoding Protein Phosphatase 2 catalytic subunit alpha, and which modulate the expression of Protein Phosphatase 2 catalytic subunit alpha. Pharmaceutical and other compositions comprising the compounds of the invention are also provided. Further provided are methods of modulating the expression of Protein Phosphatase 2 catalytic subunit alpha in cells or tissues comprising contacting said cells or tissues with one or more of the antisense compounds or compositions of the invention. Further provided are methods of treating an animal, particularly a human, suspected of having or being prone to a disease or condition associated with expression of Protein Phosphatase 2 catalytic subunit alpha by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding Protein Phosphatase 2 catalytic subunit alpha, ultimately modulating the amount of Protein Phosphatase 2 catalytic subunit alpha produced. This is accomplished by providing antisense compounds which specifically hybridize with one or more nucleic acids encoding Protein Phosphatase 2 catalytic subunit alpha. As used herein, the terms "target nucleic acid" and "nucleic acid encoding Protein Phosphatase 2 catalytic subunit alpha" encompass DNA encoding Protein Phosphatase 2 catalytic subunit alpha, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of Protein Phosphatase 2 catalytic subunit alpha. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding Protein Phosphatase 2 catalytic subunit alpha. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding Protein Phosphatase 2 catalytic subunit alpha, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'–5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood-in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed-by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have-excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—CH— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, CF, OCF, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'—O—(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., Antisense Research and Applications, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 30 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., Nucl. Acids Res., 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby. greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of Protein Phosphatase 2 catalytic subunit alpha is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding Protein Phosphatase 2 catalytic subunit alpha, enabling sandwich and other assays to easily be constructed to exploit this fact. Hybridization of the antisense oligonucleotides of the invention with a nucleic acid encoding Protein Phosphatase 2 catalytic subunit alpha can be detected by means known in the art. Such means may include conjugation of an enzyme to the oligonucleotide, radiolabelling of the oligonucleotide or any other suitable detection means. Kits using such detection means for detecting the level of Protein Phosphatase 2 catalytic subunit alpha in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, almitic acid, stearic acid, linoleic acid, linolenic acid, icaprate, tricaprate, monoolein, dilaurin, glyceryl 1-onocaprate, 1-dodecylazacycloheptan-2-one, an acylcarnitine, an acylcholine, or a monoglyceride, a diglyceride or a harmaceutically acceptable salt thereof (e.g. sodium). Also refered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. applications Ser. No. 08/886,829 (filed Jul. 1, 1997), Ser. No. 09/108,673 (filed Jul. 1, 1998), 09/256,515 (filed Feb. 23, 1999), Ser. No. 09/082,624 (filed May 21, 1998) and 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 Wm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) organ oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245;. Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (P0310), hexaglycerol pentaoleate (P0500), decaglycerol monocaprate (MCA750), decaglycerol monooleate (M0750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized"liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews*

*in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or.any other-pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal-silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention; such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-Alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabino-furanosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(Beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.9.8 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-o-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol),and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at –10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness . The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Arninooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy)ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid-forms which is collected to give the title compound as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-(2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation-by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. , 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated NH$_4$OH at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACEL™ MDQ) or., for individually prepared samples, on a commercial CE apparatus (e.g., Beckman P/ACET™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate-were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, VA). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md). Cells were routinely passaged by trypsinization and dilution when they reached 90% confluence.

NHDF Cells:

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

A10 Cells:

The rat aortic smooth muscle cell line A10 was obtained from the American Type Culure Collection (Manassas, Va.). A10 cells were routinely cultured in DMEM, high glucose (American Type Culure Collection, Manassas, Va.) supplemented with 10% fetal calf serum (Gibco/Life Technologies, Gaithersburg, Md.). Cells were routinely passaged by trypsinization and dilution when they reached 80% confluence. Cells were seeded into 96-well plates (Falcon-Primaria #3872) at a density of 2500 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 80% confluency, they were treated with oligonucleotide. For cells grown in 96-well plates, wells were washed once with 200 $\mu$L OPTI-MEMIM™-1 reduced-serum medium (Gibco BRL) and then treated with 130 $\mu$L of OPTI-MEM™-1 containing 3.75 $\mu$g/mL LIPO-FECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not-achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Protein Phosphatase 2 Catalytic Subunit Alpha Expression Antisense modulation of Protein Phosphatase 2 catalytic subunit alpha expression can be assayed in a variety of ways known in the art. For example, Protein Phosphatase 2 catalytic subunit alpha mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of Protein Phosphatase 2 catalytic subunit alpha can be quantitated in a variety of ways well known in the art, such as immunoprecipitation, Western blot analysis (immunoblotting), ELISA or fluorescence-activated cell sorting (FACS). Antibodies directed to Protein Phosphatase 2 catalytic subunit alpha can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1–11.2.22, John Wiley & Sons, Inc., 1991.

Example 11

Poly(A)+ mRNA Isolation

Poly(A)+ mRNA was isolated according to Miura et al., Clin. Chem., 1996, 42, 1758–1764. Other methods for poly(A)+ mRNA isolation are taught in, for example, Ausubel, F. M. et al., *Current Protocols in Molecular Biology*, Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the-plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of Protein Phosphatase 2 Catalytic subunit Alpha mRNA Levels Quantitation of Protein Phosphatase 2 catalytic subunit alpha mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end-of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 μL PCR cocktail (1×TAQMAN™ buffer A, 5.5 mM MgCl$_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 μL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 μL of RiboGreen™ working reagent (RiboGreen™ reagent diluted 1:2865 in 10 mM Tris-HCl, 1 mM EDTA, pH 7.5) is pipetted into a 96-well plate containing 25 μL purified, cellular RNA. The plate is read in a CytoFluor 4000 (PE Applied Biosystems) with excitation at 480 nm and emission at 520 nm.

Probes and primers to human Protein Phosphatase 2 catalytic subunit alpha were designed to hybridize to a human Protein Phosphatase 2 catalytic subunit alpha sequence, using published sequence information (GenBank accession number M60483, incorporated herein as SEQ ID NO:3). For human Protein Phosphatase 2 catalytic subunit alpha the PCR primers were:

forward primer: CACTGGATCATATCAGAGCACT-TGA (SEQ ID NO: 4)

reverse primer: CCACAGCAAGTCACACATTGG (SEQ ID NO: 5) and the PCR probe was: FAM-CGCCTACAAGAAGTTCCCCATGAGGG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were:

forward primer: GAAGGTGAAGGTCGGAGTC (SEQ ID NO: 7)

reverse primer: GAAGATGGTGATGGGATTTC (SEQ ID NO: 8) and the PCR probe was: 5' JOE-CAAGCTTCCCGTTCTCAGCCX-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse Protein Phosphatase 2 catalytic subunit alpha were designed to hybridize to a mouse Protein Phosphatase 2 catalytic subunit alpha sequence, using published sequence information (GenBank accession number AF076192, incorporated herein as SEQ ID NO:10). For mouse Protein Phosphatase 2 catalytic subunit alpha the PCR primers were:

forward primer: TCAACAGCCGTGACCACTTTAG (SEQ ID NO:11)

reverse primer: CGCTATGCCAGAAACTGGATTC (SEQ ID NO: 12) and the PCR probe was: FAM-CCAGTTCATTGCATGCTGACGCGA-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were:

forward primer: GGCAAATTCAACGGCACAGT (SEQ ID NO: 14)

reverse primer: GGGTCTCGCTCCTGGAAGAT (SEQ ID NO: 15) and the PCR probe was: 5' JOE-AAGGCCGAGAATGGGAAGCTTGTCATCX-TAMRA 3' (SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of Protein Phosphatase 2 Catalytic Subunit Alpha mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human Protein Phosphatase 2 catalytic subunit alpha, a human Protein Phosphatase 2 catalytic subunit alpha specific probe was prepared by PCR using the forward primer CACTGGATCATATCAGAGCACTTGA (SEQ ID NO: 4) and the reverse primer CCACAGCAAGTCACA-CATTGG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse Protein Phosphatase 2 catalytic subunit alpha, a mouse Protein Phosphatase 2 catalytic subunit alpha specific probe was prepared by PCR using the forward primer TCAACAGCCGTGACCACTTTAG (SEQ ID NO:11) and the reverse primer CGCTATGCCA-GAAACTGGATTC (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human Protein Phosphatase 2 Catalytic Subunit Alpha Expression by Chimeric Phosphorothioate Oligonucleotides Having 2'-MOE Wings and a Deoxy Gap In accordance with the present invention, a series of oligonucleotides were designed to target different regions of the human Protein Phosphatase 2 catalytic subunit alpha RNA, using published sequences (GenBank accession number M60483, incorporated herein as SEQ ID NO: 3, GenBank accession number NM_002715, incorporated herein as SEQ ID NO: 17, and residues 10001–50000 from the complement of GenBank accession number AC007199.1, incorporated herein as SEQ ID NO: 18). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The 15 internucleoside (backbone) linkages are phosphorothioate (P=S) throughout the oligonucleotide. All cytidine residues are 5-methylcytidines. The compounds were analyzed for their effect on human Protein Phosphatase 2 catalytic subunit alpha mRNA levels by quantitative real-time PCR as described in other examples herein. Data are averages from two experiments. If present, "N.D." indicates "no data".

TABLE 1

Inhibition of human Protein Phosphatase 2 :catalytic subunit alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 110160 | Coding | 3 | 1451 | accaaggcagtgagaggaag | 58 | 19 |
| 110169 | 3'UTR | 3 | 2627 | caccagtcttgcccattgat | 57 | 20 |
| 118885 | 5'UTR | 17 | 10 | ctcgctgaggctccagagct | 58 | 21 |
| 118886 | 5'UTR | 17 | 55 | ctctcaccgcagtactcggc | 70 | 22 |
| 118887 | 5'UTR | 17 | 100 | ctcgtgtacttctggcggct | 64 | 23 |
| 118888 | 5'UTR | 17 | 124 | acacgcacacgccgccgccg | 79 | 24 |
| 118889 | 5'UTR | 17 | 152 | tcccgcgccgccgcccgcac | 68 | 25 |
| 118890 | Coding | 17 | 279 | ctcttgacctgggactcgga | 80 | 26 |
| 118891 | Coding | 17 | 305 | ggatttctttagccttctcg | 51 | 27 |
| 118892 | Coding | 17 | 315 | tcttttgtcaggatttcttt | 64 | 28 |
| 118893 | Coding | 17 | 489 | agcagtgtaactgtttcaac | 53 | 29 |
| 118894 | Coding | 17 | 499 | aagagctacaagcagtgtaa | 52 | 30 |
| 118895 | Coding | 17 | 509 | aacgaaccttaagagctaca | 62 | 31 |
| 118896 | Coding | 17 | 564 | tgtgtgatctgtctgctctc | 72 | 32 |
| 118897 | Coding | 17 | 621 | ttccaaacatttgcatttcc | 78 | 33 |
| 118898 | Coding | 17 | 676 | ctgcccatccaccaaggcag | 40 | 34 |
| 118899 | Coding | 17 | 686 | gacagaagatctgcccatcc | 49 | 35 |
| 118900 | Coding | 17 | 782 | agtcacacattggaccctca | 82 | 36 |
| 118901 | Coding | 17 | 792 | gaccacagcaagtcacacat | 71 | 37 |

TABLE 1-continued

Inhibition of human Protein Phosphatase 2 :catalytic subunit
alpha mRNA levels by chimeric phosphorothioate
oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 118902 | Coding | 17 | 877 | attaaatgtctcagaaatat | 25 | 38 |
| 118903 | Coding | 17 | 895 | cgtgaggccattggcatgat | 57 | 39 |
| 118904 | Coding | 17 | 939 | cagttatatcctccatcac | 44 | 40 |
| 118905 | Coding | 17 | 984 | tagtttggagcactgaaaat | 67 | 41 |
| 118906 | Coding | 17 | 1012 | tgcagcttggttaccacaac | 68 | 42 |
| 118907 | Coding | 17 | 1022 | gttccatgattgcagcttgg | 72 | 43 |
| 118908 | Coding | 17 | 1080 | tcgcctctacgaggtgctgg | 57 | 44 |
| 118909 | Stop Codon | 17 | 1122 | cattacaggaagtagtctgg | 57 | 45 |
| 118910 | 3'UTR | 17 | 1152 | tcatggcaatactgtacaag | 63 | 46 |
| 118911 | 3'UTR | 17 | 1159 | atatggttcatggcaatact | 58 | 47 |
| 118912 | 3'UTR | 17 | 1207 | ctgacactttggagttactg | 48 | 48 |
| 118913 | 3'UTR | 17 | 1214 | ctattttctgacactttgga | 66 | 49 |
| 118914 | 3'UTR | 17 | 1261 | atggcacatctttggtcca | 74 | 50 |
| 118915 | 3'UTR | 17 | 1262 | tatggcacatctttggtcc | 60 | 51 |
| 118916 | 3'UTR | 17 | 1284 | gacaagaggctttgtatttt | 70 | 52 |
| 118917 | 3'UTR | 17 | 1294 | ggctgttgatgacaagaggc | 67 | 53 |
| 118918 | 3'UTR | 17 | 1304 | aagtggtcacggctgttgat | 66 | 54 |
| 118919 | 3'UTR | 17 | 1309 | ttctaaagtggtcacggctg | 68 | 55 |
| 118920 | 3'UTR | 17 | 1314 | gttcattctaaagtggtcac | 74 | 56 |
| 118921 | 3'UTR | 17 | 1324 | caatgaactggttcattcta | 65 | 57 |
| 118922 | 3'UTR | 17 | 1353 | ttcttgaccaacaatgtcgc | 68 | 58 |
| 118923 | 3'UTR | 17 | 1364 | cagaaactggtttcttgacc | 67 | 59 |
| 118924 | 3'UTR | 17 | 1374 | agcgctatgccagaaactgg | 56 | 60 |
| 118925 | 3'UTR | 17 | 1384 | aactacaaatagcgctatgc | 54 | 61 |
| 118926 | 3'UTR | 17 | 1394 | aagcaaaagtaactacaaat | 25 | 62 |
| 118927 | 3'UTR | 17 | 1419 | cttattatctgcagtctctc | 78 | 63 |
| 118928 | 3'UTR | 17 | 1431 | taatgtttacatcttattat | 28 | 64 |
| 118929 | 3'UTR | 17 | 1492 | tctacagtcatgctgagtaa | 86 | 65 |
| 118930 | 3'UTR | 17 | 1522 | agctccaatgattgtttgct | 78 | 66 |
| 118931 | 3'UTR | 17 | 1529 | ttcattaagctccaatgatt | 58 | 67 |
| 118932 | 3'UTR | 17 | 1532 | atgttcattaagctccaatg | 66 | 68 |
| 118933 | 3'UTR | 17 | 1710 | tcaaaacaactcaccaggtt | 65 | 69 |
| 118934 | 3'UTR | 17 | 1720 | acagttctgttcaaaacaac | 46 | 70 |
| 118935 | 3'UTR | 17 | 1830 | ccattgatacaattaaaatt | 9 | 71 |
| 118936 | 3'UTR | 17 | 1998 | aattgtaatatgtgaaatac | 12 | 72 |
| 118937 | 3'UTR | 17 | 2017 | gcacaccaacaatgtgacaa | 37 | 73 |
| 118938 | 3'UTR | 17 | 2029 | aacccacaaagtgcacacca | 54 | 74 |
| 118939 | 3'UTR | 17 | 2033 | gaagaacccacaaagtgcac | 57 | 75 |
| 118940 | 3'UTR | 17 | 2121 | aacccacaaagtgcacacca | 42 | 76 |
| 118941 | Intron | 18 | 2946 | aagtgacgtgctgcaaagtt | 48 | 77 |
| 118942 | Intron | 18 | 5354 | agtctttgggttgcatctgt | 56 | 78 |
| 118943 | Intron | 18 | 5878 | atgaataggaagctttcaag | 48 | 79 |
| 118944 | Intron | 18 | 6840 | acccagtctcttagttttcc | 58 | 80 |
| 118945 | Intron | 18 | 8584 | tccaggcgtgagccactgtg | 66 | 81 |
| 118946 | Intron | 18 | 8824 | gctgtcgcttaggctggagt | 42 | 82 |
| 118947 | Intron | 18 | 10523 | gggcgaagtggctcacgcct | 36 | 83 |
| 118948 | Intron | 18 | 11582 | agctgagagcagcaagtggc | 54 | 84 |
| 118949 | Intron | 18 | 12591 | agcttctttttatatcagca | 60 | 85 |
| 118950 | Intron | 18 | 14058 | acacaccaaaacccatctc | 32 | 86 |
| 118951 | Intron | 18 | 14626 | ataaaggctaatagaggtga | 40 | 87 |
| 118952 | Intron | 18 | 14682 | acattcgcttaaaagccaaa | 39 | 88 |
| 118953 | Intron | 18 | 18442 | ttgacattatcaaattgtcc | 55 | 89 |
| 118954 | Intron | 18 | 20970 | gtgcagtagtatgatcatag | 41 | 90 |
| 118955 | Intron | 18 | 22349 | aatatgctcactttgtcctg | 33 | 91 |
| 118956 | Intron | 18 | 24971 | cagtggtttgttccttttca | 60 | 92 |
| 118957 | Intron | 18 | 26237 | tggccctctggtgtttctg | 32 | 93 |
| 118958 | Intron | 18 | 27397 | acatgttaatggattcattg | 31 | 94 |
| 118959 | Intron | 18 | 28742 | cgaactcctgatctcaggtg | 22 | 95 |
| 118960 | Intron | 18 | 28994 | aaataaaagttggaatctga | 0 | 96 |

As shown in Table 1, SEQ ID NOs 19, 20, 21, 22, 23, 24, 25, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 63, 65, 66, 67, 68, 69, 70, 74, 75, 76, 77, 78, 79, 80, 81, 82, 84, 85, 87, 89, 90 and 92 demonstrated at least 40% inhibition of human Protein Phosphatase 2 catalytic subunit alpha expression in this assay and are therefore preferred. The target sites to which these preferred sequences are complementary are herein referred to as "active sites" and are therefore preferred sites for targeting by compounds of the present invention.

Example 16
Antisense Inhibition of Mouse Protein Phosphatase 2 Catalytic Subunit Alpha Expression by Chimeric Phosphorothioate Oligonucleotides Having 2'-MOE Wings and a Deoxy Gap In accordance with the present invention, a second series of oligonucleotides were designed to target different regions of the mouse Protein Phosphatase 2 catalytic subunit alpha RNA, using published sequences (GenBank accession number AF076192, incorporated herein as SEQ ID NO: 10). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse Protein Phosphatase 2 catalytic subunit alpha mRNA levels by quantitative real-time PCR as described in other examples herein. Data are averages from two experiments. If present, "N.D." indicates "no data".

As shown in Table 2, SEQ ID NOs 19, 24, 25, 26, 27, 28, 29, 30, 31, 32, 33, 34, 35, 36, 37, 39, 40, 41, 42, 43, 44, 45, 46, 48, 49, 51, 52, 53, 54, 55, 56, 57, 58, 60, 61, 65, 66, 67, 68, 69 and 70 demonstrated at least 40% inhibition of mouse Protein Phosphatase 2 catalytic subunit alpha expression in this experiment and are therefore preferred. The target sites to which these preferred sequences are complementary are herein referred to as "active sites" and are therefore preferred sites for targeting by compounds of the present invention.

Example 17

Western Blot Analysis of Protein Phosphatase 2 Catalytic Subunit Alpha Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes

TABLE 2

Inhibition of mouse Protein Phosphatase 2 catalytic subunit alpha mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 110160 | Coding | 10 | 652 | accaaggcagtgagaggaag | 68 | 19 |
| 118888 | 5'UTR | 10 | 111 | acacgcacacgccgccgccg | 75 | 24 |
| 118889 | 5'UTR | 10 | 138 | tcccgccgccgccccgcac | 85 | 25 |
| 118890 | Coding | 10 | 265 | ctcttgacctgggactcgga | 70 | 26 |
| 118891 | Coding | 10 | 291 | ggatttctttagccttctcg | 40 | 27 |
| 118892 | Coding | 10 | 301 | tcttttgtcaggatttcttt | 76 | 28 |
| 118893 | Coding | 10 | 475 | agcagtgtaactgtttcaac | 44 | 29 |
| 118894 | Coding | 10 | 485 | aagagctacaagcagtgtaa | 58 | 30 |
| 118895 | Coding | 10 | 495 | aacgaaccttaagagctaca | 54 | 31 |
| 118896 | Coding | 10 | 550 | tgtgtgatctgtctgctctc | 70 | 32 |
| 118897 | Coding | 10 | 607 | ttccaaacatttgcatttcc | 94 | 33 |
| 118898 | Coding | 10 | 662 | ctgcccatccaccaaggcag | 64 | 34 |
| 118899 | Coding | 10 | 672 | gacagaagatctgcccatcc | 54 | 35 |
| 118900 | Coding | 10 | 768 | agtcacacattggaccctca | 80 | 36 |
| 118901 | Coding | 10 | 778 | gaccacagcaagtcacacat | 69 | 37 |
| 118902 | Coding | 10 | 863 | attaaatgtctcagaaatat | 13 | 38 |
| 118903 | Coding | 10 | 881 | cgtgaggccattggcatgat | 53 | 39 |
| 118904 | Coding | 10 | 925 | cagttatatccctccatcac | 51 | 40 |
| 118905 | Coding | 10 | 970 | tagtttggagcactgaaaat | 74 | 41 |
| 118906 | Coding | 10 | 998 | tgcagcttggttaccacaac | 78 | 42 |
| 118907 | Coding | 10 | 1008 | gttccatgattgcagcttgg | 88 | 43 |
| 118908 | Coding | 10 | 1066 | tcgcctctacgaggtgctgg | 81 | 44 |
| 118909 | Stop Codon | 10 | 1108 | cattacaggaagtagtctgg | 59 | 45 |
| 118910 | 3'UTR | 10 | 1138 | tcatggcaatactgtacaag | 65 | 46 |
| 118912 | 3'UTR | 10 | 1193 | ctgacactttggagttactg | 56 | 48 |
| 118913 | 3'UTR | 10 | 1200 | ctattttctgacactttgga | 46 | 49 |
| 118915 | 3'UTR | 10 | 1247 | tatggcacatcttttggtcc | 61 | 51 |
| 118916 | 3'UTR | 10 | 1268 | gacaagaggctttgtatttt | 71 | 52 |
| 118917 | 3'UTR | 10 | 1278 | ggctgttgatgacaagaggc | 58 | 53 |
| 118918 | 3'UTR | 10 | 1288 | aagtggtcacggctgttgat | 82 | 54 |
| 118919 | 3'UTR | 10 | 1293 | ttctaaagtggtcacggctg | 88 | 55 |
| 118920 | 3'UTR | 10 | 1298 | gttcattctaaagtggtcac | 92 | 56 |
| 118921 | 3'UTR | 10 | 1308 | caatgaactggttcattcta | 55 | 57 |
| 118922 | 3'UTR | 10 | 1337 | ttcttgaccaacaatgtcgc | 93 | 58 |
| 118924 | 3'UTR | 10 | 1358 | agcgctatgccagaaactgg | 84 | 60 |
| 118925 | 3'UTR | 10 | 1368 | aactacaaatagcgctatgc | 70 | 61 |
| 118926 | 3'UTR | 10 | 1378 | aagcaaaagtaactacaaat | 18 | 62 |
| 118929 | 3'UTR | 10 | 1469 | tctacagtcatgctgagtaa | 72 | 65 |
| 118930 | 3'UTR | 10 | 1496 | agctccaatgattgtttgct | 69 | 66 |
| 118931 | 3'UTR | 10 | 1503 | ttcattaagctccaatgatt | 66 | 67 |
| 118932 | 3'UTR | 10 | 1506 | atgttcattaagctccaatg | 78 | 68 |
| 118933 | 3'UTR | 10 | 1664 | tcaaaacaactcaccaggtt | 59 | 69 |
| 118934 | 3'UTR | 10 | 1674 | acagttctgttcaaaagaac | 58 | 70 | and loaded on a 16% SDS-PAGE gel. Gels are run for 1.5 hours at 150 V, and transferred to membrane for western blotting. Appropriate primary antibody directed to Protein Phosphatase 2 catalytic subunit alpha is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to nucleobases 10 through 29, nucleobases 55 through 74, or nucleobases 124 through 143 of a 5'-untranslated region, nucleobases 279 through 1099 of a coding region, or nucleobases 1152 through 2140 of a 3'-untranslated region of a nucleic acid molecule encoding human Protein Phosphatase 2 catalytic subunit alpha of SEQ ID NO: 17, an intron region of a nucleic acid molecule encoding human Protein Phosphatase 2 catalytic subunit alpha of SEQ ID NO: 18, nucleobases 111 through 130 of a 5'-untranslated region, nucleobases 265 through 284, nucleobases 291 through 320, nucleobases 475 through 514, nucleobases 550 through 569, nucleobases 607 through 626, nucleobases 662 through 691, nucleobases 768 through 797, nucleobases 863 through 900, nucleobases 925 through 944, nucleobases 970 through 989, nucleobases 998 through 1027, or nucleobases 1066 through 1085 of a coding region, or nucleobases 1138 through 1693 of a 3'-untranslated region of a nucleic acid molecule encoding mouse Protein Phosphatase 2 catalytic subunit alpha of SEQ ID NO: 10, wherein said compound specifically hybridizes with one of said regions and inhibits the expression of one of said human of mouse Protein Phosphatase 2 catalytic subunit alpha nucleic acid molecules.

2. The compound of claim 1 which is an antisense oligonucleotide.

3. A compound up to 50 nucleobases in length comprising at least an 8 nucleobase portion of SEQ ID NO: 20, 21, 22, 24, 26, 27, 28, 29, 30, 31, 32, 33, 34, 35, 36, 37, 39, 40, 41, 42, 43, 44, 45, 46, 47, 48, 49, 50, 51, 52, 53, 54, 55, 56, 57, 58, 59, 60, 61, 63, 65, 66, 67, 68, 69, 70, 74, 75, 76, 77, 78, 79, 80, 81, 82, 84, 85, 87, 89, 90 or 92 which inhibits the expression of human or mouse Protein Phosphatase 2 catalytic subunit alpha.

4. The compound of claim 2 wherein the antisense oligonucleotide comprises at least one modified internucleoside linkage.

5. The compound of claim 4 wherein the modified internucleoside linkage is a phosphorothioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A composition comprising the compound of claim 1 and a pharmaceutically acceptable carrier or diluent.

12. The composition of claim 11 further comprising a colloidal dispersion system.

13. The composition of claim 11 wherein the compound is an antisencse oligonucleotide.

14. A method of inhibiting the expression of human or mouse Protein Phosphatase 2 catalytic subunit alpha in cells or tissues comprising contacting said cells or tissues in vitro with the compound of claim 1 so that expression of human or mouse Protein Phosphatase 2 catalytic subunit alpha is inhibited.

15. The compound of claim 3 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonuicleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 3 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of human or mouse Protein Phosphatase 2 catalytic subunit alpha in cells or tissues comprising contacting said cells or tissues in vitro with the compound of claim 3 so that expression of human or mouse Protein Phosphatase 2 catalytic subunit alpha is inhibited.

* * * * *